(12) United States Patent
Hunter et al.

(10) Patent No.: US 12,016,739 B2
(45) Date of Patent: Jun. 25, 2024

(54) SYSTEMS AND METHODS FOR CAPTURING, DISPLAYING, AND MANIPULATING MEDICAL IMAGES AND VIDEOS

(71) Applicant: Stryker Corporation, Kalamazoo, MI (US)

(72) Inventors: Brandon Hunter, Hollister, CA (US); Ramanan Paramasivan, San Jose, CA (US); Amit A. Mahadik, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 18/171,324

(22) Filed: Feb. 17, 2023

(65) Prior Publication Data

US 2023/0190404 A1  Jun. 22, 2023

Related U.S. Application Data

(62) Division of application No. 17/507,712, filed on Oct. 21, 2021, now Pat. No. 11,586,837.

(Continued)

(51) Int. Cl.
*A61B 90/00* (2016.01)
*G06V 10/10* (2022.01)
*G16H 30/00* (2018.01)

(52) U.S. Cl.
CPC .............. *A61B 90/37* (2016.02); *G06V 10/16* (2022.01); *G16H 30/00* (2018.01); *G06F 2218/08* (2023.01)

(58) Field of Classification Search
None
See application file for complete search history.

(56) References Cited

U.S. PATENT DOCUMENTS 6,128,002 A * 10/2000 Leiper .................... G16H 30/40
345/161
6,184,862 B1 * 2/2001 Leiper .................... G16H 30/20
345/161

(Continued)

FOREIGN PATENT DOCUMENTS

WO  2011/113483 A1  9/2011
WO  2020/113030 A1  6/2020

OTHER PUBLICATIONS

Hunter et al., U.S. Notice of Allowance and Fee(s) Due dated Oct. 18, 2022, directed to U.S. Appl. No. 17/507,712; 8 pages.

(Continued)

*Primary Examiner* — Soo Shin
(74) *Attorney, Agent, or Firm* — Morrison & Foerster LLP

(57) ABSTRACT

A surgical image capture and display system includes a handheld image capture and pointing device and a display assembly. An image is captured by an image sensor of the handheld device and displayed on the display assembly. The image sensor detects light emitted by one or more beacons of the display assembly. The system determines, based on the light emitted by the one or more beacons, a position or orientation of the handheld device relative to the display assembly. The system updates display of a graphical user interface comprising the image on the display assembly in accordance with the determined position or orientation of the handheld device.

10 Claims, 14 Drawing Sheets
(1 of 14 Drawing Sheet(s) Filed in Color)

Related U.S. Application Data

(60) Provisional application No. 63/104,266, filed on Oct. 22, 2020.

(56) References Cited

U.S. PATENT DOCUMENTS

| | | | |
|---|---|---|---|
| 7,050,845 | B2 | 5/2006 | Vilsmeier |
| 7,846,107 | B2 | 12/2010 | Hoffman et al. |
| 2007/0073137 | A1 | 3/2007 | Schoenefeld |
| 2008/0319275 | A1* | 12/2008 | Chiu .................. A61B 5/0002 600/300 |
| 2014/0107471 | A1 | 4/2014 | Haider et al. |
| 2014/0171764 | A1* | 6/2014 | Kim .................. A61B 1/000094 600/317 |
| 2016/0135762 | A1* | 5/2016 | Mihailescu .......... A61B 6/4057 600/424 |
| 2016/0364878 | A1* | 12/2016 | Guo .................. G02B 27/0172 |
| 2017/0360412 | A1* | 12/2017 | Rothberg ................ A61B 8/46 |
| 2019/0192229 | A1* | 6/2019 | Berlin .................. A61B 8/5246 |
| 2019/0251389 | A1* | 8/2019 | Guo .......................... G06T 7/187 |
| 2019/0290297 | A1 | 9/2019 | Haider et al. |
| 2020/0226414 | A1* | 7/2020 | Guo .......................... G06T 7/11 |
| 2022/0132026 | A1 | 4/2022 | Hunter et al. |
| 2022/0296914 | A1 | 9/2022 | Tsumatori |
| 2022/0317827 | A1 | 10/2022 | Paramasivan et al. |
| 2022/0321227 | A1 | 10/2022 | Wakana |

OTHER PUBLICATIONS

Hunter et al., U.S. Restriction Requirement dated May 4, 2022, directed to U.S. Appl. No. 17/507,712; 6 pages.

International Preliminary Report on Patentability dated Apr. 13, 2023, directed to International Application No. PCT/US2021/071977; 12 pages.

International Search Report and Written Opinion dated Apr. 4, 2022, directed to International Application No. PCT/US2021/071977; 19 pages.

Invitation to Pay Additional Fees and, Where Applicable, Protest Fee dated Feb. 10, 2022, directed to International Application No. PCT/US2021/071977; 13 pages.

Jacobson et al. (Mar. 2012). "In vivo testing of a prototype system providing simultaneous white light and near infrared autofluorescence image acquisition for detection of bladder cancer," Journal of Biomedical Optics, 17(3): 036011-1-036011-6.

* cited by examiner

SYSTEMS AND METHODS FOR CAPTURING, DISPLAYING, AND MANIPULATING MEDICAL IMAGES AND VIDEOS

CROSS-REFERENCE TO RELATED APPLICATIONS

This application is a divisional of U.S. patent application Ser. No. 17/507,712, filed Oct. 21, 2021, which claims the benefit of U.S. Provisional Application No. 63/104,266, filed Oct. 22, 2020, the entire contents of which are hereby incorporated by reference herein.

FIELD

The present disclosure relates generally to medical imaging systems, and more specifically systems and methods for capturing, displaying, and manipulating medical images and videos.

BACKGROUND

Capturing and displaying medical and surgical images is integral to many medical and surgical procedures. According to known techniques, medical images and videos may be captured by image sensors of one or more cameras and then displayed on computer monitors or dedicated display screens. According to known techniques, medical images and videos may be manipulated using a mouse, keyboard, or touch-screen controls.

SUMMARY

As explained above, according to known techniques, medical images and videos are captured by image sensors of various cameras, displayed on computer monitors or dedicated display screens, and manipulated using a mouse, keyboard, or touch-screen controls. However, known techniques for capturing, displaying, and manipulating medical images and videos are cumbersome and inconvenient for surgeons and other medical practitioners. For example, a practitioner who wishes to capture one or more images or video frames and then display and manipulate the image may be required to use a camera to capture the image/video, then put down the camera and use another input device such as a mouse, keyboard, or touch-screen display to manipulate the captured image. The requirement to use a different device to capture the image and to manipulate the captured image introduces delay and the potential for contamination between the various devices. Accordingly, there is a need for improved systems and methods for capturing, displaying, and manipulating medical images and video, particularly methods and systems that obviate the need for a practitioner to use multiple different devices to capture images/video and to manipulate the captured images/video.

Disclosed herein are systems, methods, and techniques for capturing, displaying, and manipulating medical images and videos. A handheld image capture and pointing device may include one or more image sensors configured to capture both white light video/images and infrared video/images. (As used herein, "infrared" or "IR" may refer to infrared and/or near-infrared ("NIR") light.) The handheld image capture and pointing device may be aimed at a region of tissue of a patient and the one or more image sensors may capture a series of video frames in white light and a series of video frames in infrared light. An image from one of the captured video frames may be displayed on a display of a display assembly, wherein the display assembly comprises one or more infrared beacons positioned proximate to the display assembly and configured to emit infrared light. After capturing the image with the handheld device, and while the image is displayed on the display assembly, the operator may aim the handheld device at the display assembly such that the infrared beacons are within the field of vision of the handheld device and such that the infrared light emitted by the beacons is detected by one or more of the image sensors of the device. Based on the infrared light detected by the device, a processor associated with the system may determine a position and/or orientation of the handheld device relative to the display assembly, and the system may cause a graphical user interface including the displayed image to be updated in accordance with the determined position and/or orientation. For example, the graphical user interface may be updated by annotating the displayed image, zooming the displayed image or scaling the size of an annotation on the image, rotating the displayed image or an annotation on the image, or the like. Thus, the user of the handheld image capture and pointing device may be able to use a single device both to capture medical images and to manipulate the images while they are displayed, obviating the need to frequently switch between different devices during medical procedures.

Furthermore, known techniques for extracting information from medical video streams require manual input and are imprecise and cumbersome. For example, an IR video stream may have little visible information when a fluorescence agent is not present in the vasculature of the tissue depicted, and it may therefore be difficult for a system or user to select a region of a frame of the IR video stream on which to focus before the arrival of the fluorescence agent. Accordingly, there is a need for improved systems for extracting information from medical video streams, including for selecting regions of frames of medical video streams on which image analysis and/or visualization should be performed.

Disclosed herein are systems, methods, and techniques for using frame-synchronized object tracking to identify regions of medical video streams for analysis and/or visualization. A system for medical image capture, display, manipulation, annotation, and analysis may be configured such that two (or more) video streams depicting the same target tissue may be simultaneously captured, wherein a first one of the video streams captures the target tissue in a first spectrum (e.g., white light) and a second one of the video streams captures the target tissue in a second spectrum (e.g., IR). An object such as a tissue feature may be tracked in one video stream (e.g., a white light video stream) to determine a location of the other video stream (e.g., an IR video stream) at which image analysis should be performed or from which data should be extracted. In this manner, a system may be configured to use frame-synchronized video channels (e.g., video streams) to extract information out of a first channel of video (e.g., a white light video channel) and apply that information to corresponding positions in the second channel of video (e.g., an IR video channel).

Furthermore, known techniques for annotating and tracking tissue samples comprise multiple manual steps and are error prone. During a medical procedure, a surgeon or other medical practitioner may take tissue samples from various parts of the anatomy. These tissue samples may then be sent to pathology for analysis. After the analysis reports are obtained, the surgeon then has to correlate multiple pathology results to the tissue samples that were taken. This process is done manually and is prone to errors. Accordingly, there is a need for improved systems and methods for marking different regions of anatomy with labels during the procedure, saving those annotations as part of video, and tracking pathology results associated with those regions of anatomy.

Disclosed herein are systems, methods, and techniques for capturing medical images and generating annotation data to be stored in association with a region of interest in the medical image and/or in association with a tissue sample extracted from the tissue at an area indicated by the region of interest in the image. A system may capture a medical image (e.g., a frame from a medical video) using a handheld image capture and pointing device, display said medical image on a display assembly, determine a location in said image displayed on said display assembly at which the handheld device is pointed, and generate and store annotation data associated with a region of interest defined in the image at the location at which the handheld device is pointed.

According to an aspect, a surgical image capture and display system is provided, the surgical image capture and display system comprising: a handheld image capture and pointing device, the handheld device comprising an image sensor configured to detect white light and infrared light; a display assembly configured to display one or more images captured by the handheld device; and one or more processors configured to cause the system to: capture, by the image sensor of the handheld device, an image; display, by a display of the display assembly, a graphical user interface comprising the image; while the graphical user interface is displayed by the display, detect, by the image sensor, light emitted by one or more beacons of the display assembly; determine, based on the light emitted by the one or more beacons of the display assembly, a position or orientation of the handheld device relative to the display assembly; and update display of the graphical user interface comprising the image in accordance with the position or orientation of the handheld device.

Optionally, determining the position or orientation comprises determining a distance from the display assembly to the handheld device.

Optionally, determining the position or orientation comprises determining an offset angle of the handheld device with respect to a plane intersecting the display assembly at a right angle along a line from the top center of the display assembly to the bottom center of the display assembly.

Optionally, determining the position or orientation comprises determining both the position and the orientation of the handheld device.

Optionally, determining the position or orientation comprises determining a location on the display at which the handheld device is aimed.

Optionally, determining the orientation comprises determining a rotational orientation of the handheld device with respect to a line along which the handheld device is aimed.

Optionally, capturing the image is performed prior to detecting the light emitted by the one or more beacons.

Optionally, the system is configured to operate in an image capture mode in which the image is captured and stored by the system; and the system is configured to operate in an image manipulation mode in which the image is displayed on the display and the graphical user interface accepts one or more inputs for manipulation of the image, wherein the one or more inputs are executed via the handheld device and based at least in part on the determined position or orientation of the handheld device.

Optionally, updating the graphical user interface comprises displaying a cursor on the graphical user interface at a location on the display at which the handheld device is determined to be aimed.

Optionally, updating the graphical user interface comprises generating and displaying an annotation on the displayed image at a location on the display at which the handheld device is determined to be aimed.

Optionally, updating the graphical user interface comprises rotating an image annotation in accordance with the orientation of the handheld device.

Optionally, updating the graphical user interface comprises modifying a zoom level at which the image is displayed in accordance with the position or orientation of the handheld device.

Optionally, updating the graphical user interface comprises modifying a size of an image annotation in accordance with the position or orientation of the handheld device.

Optionally, updating the graphical user interface comprises setting a font size for the graphical user interface in accordance with the position or orientation of the handheld device.

Optionally, updating the graphical user interface comprises displaying a notification based on an offset angle determined in accordance with the determined position or orientation of the handheld device.

Optionally, the one or more processors are configured to cause the system to: in accordance with the determined position or orientation of the handheld device, identify a first region of interest of the image; and apply one or more of a tracking algorithm and an image analysis algorithm to the first region of interest of the image.

Optionally, the image is captured by the image capture and pointing device in a first spectrum; and the one or more processors are configured to cause the system to: capture, by the image capture and pointing device, a second image in a second spectrum; and apply one or more of the tracking algorithm and the image analysis algorithm to a second region of interest corresponding to the first region of interest, wherein the second region of interest is in the second image.

Optionally, determining the position or orientation of the handheld device is further based on data received from a sensor onboard the handheld device, wherein the sensor comprises one or more of an accelerometer, a gyroscope, and a compass.

Optionally, determining the position or orientation of the handheld device is further based on processing video frames captured by the image sensor.

Optionally, processing video frames comprises applying an optical flow algorithm to track a direction of movement in the video frames.

Optionally, the image is captured by the image sensor as part of a time-series of video frames.

Optionally, the image is one of a white-light image and a fluorescence image.

Optionally, detecting the light emitted by the one or more beacons of the display assembly is performed by the image sensor of the handheld device.

Optionally, the light emitted by the one or more beacons is infrared light.

Optionally, the one or more beacons are positioned proximate to a periphery of the display in respective fixed locations relative to the display.

According to an aspect, a computer program product including computer implementable instructions, or a non-transitory computer-readable storage medium for surgical image capture and display is provided, the non-transitory computer-readable storage medium storing instructions. The instructions are configured to be executed by one or more processors of a surgical image capture and display system comprising (a) a handheld image capture and pointing device, the handheld device comprising an image sensor configured to detect white light and infrared light and (b) a display assembly configured to display one or more images captured by the handheld device, wherein executing the instructions causes the system to: capture, by the image sensor of the handheld device, an image; display, by a display of the display assembly, a graphical user interface comprising the image; while the graphical user interface is displayed by the display, detect, by the image sensor, light emitted by one or more beacons of the display assembly; determine, based on the light emitted by the one or more beacons of the display assembly, a position or orientation of the handheld device relative to the display assembly; and update display of the graphical user interface comprising the image in accordance with the position or orientation of the handheld device.

According to an aspect, a surgical image capture and display method is provided, the method performed at a surgical image capture and display system comprising (a) a handheld image capture and pointing device, the handheld device comprising an image sensor configured to detect white light and infrared light, (b) a display assembly configured to display one or more images captured by the handheld device, and (c) one or more processors, the method comprising: capturing, by the image sensor of the handheld device, an image; displaying, by a display of the display assembly, a graphical user interface comprising the image; while the graphical user interface is displayed by the display, detecting, by the image sensor, light emitted by one or more beacons of the display assembly; determining, based on the light emitted by the one or more beacons of the display assembly, a position or orientation of the handheld device relative to the display assembly; and updating display of the graphical user interface comprising the image in accordance with the position or orientation of the handheld device.

According to an aspect, a medical video analysis system, comprising: an image capture device configured to detect white light and infrared light; a display assembly configured to display one or more images captured by the handheld device; and one or more processors configured to cause the system to: capture a first series of video frames of target tissue in a first spectrum; capture a second series of video frames of the target tissue in a second spectrum, wherein the second series of video frames is captured simultaneously with capturing of the first series of video frames; identify a first region of interest in one or more frames of the first series of video frames, the first region of interest corresponding to a first feature of the target tissue apply a tracking algorithm to track the first feature of the target tissue in the first series of video frames, wherein the tracking algorithm is configured to track the first feature of the target tissue independently from tracking of surrounding tissue; and identify a second region of interest in one or more frames of the second series of video frames based on the tracking algorithm applied to the first series of video frames, the second region of interest corresponding to the first feature of the target tissue.

Optionally, the one or more processors are configured to cause the system to apply an image analysis algorithm to the second region of interest in the one or more frames of the second series of video frames.

Optionally, the one or more processors are configured to cause the system to visualize the second region of interest.

Optionally: the first and second series of video frames capture a first period of time during which a fluorescence dye is not present in the target tissue and a second period of time during which the fluorescence dye is present in the target tissue; the tracking algorithm is applied to a first set of frames, corresponding to both the first period of time and the second period of time, from the first series of video frames; and the one or more frames of the second series of video frames to which an image analysis algorithm are applied are corresponding to the second period of time.

Optionally, the one or more frames of the first series of video frames in which the first region of interest is identified correspond to the first period of time.

Optionally, the one or more processors are configured to cause the system to: identify a third region of interest in one or more frames of the first series of video frames, the third region of interest corresponding to a second feature of the target tissue; apply the tracking algorithm to track the second feature of the target tissue in the first series of video frames, wherein the tracking algorithm is configured to track the second feature of the target tissue independently from tracking of the surrounding tissue; and identify a fourth region of interest in one or more frames of the second series of video frames based on the tracking algorithm applied to the first series of video frames, the fourth region of interest corresponding to the second feature of the target tissue.

Optionally, the image capture device comprises a first image sensor configured to capture the video frames of the first spectrum and a second image sensor configured to capture the video frames of the second spectrum.

Optionally, the image capture device comprises a first image sensor configured to capture the video frames of the first spectrum and the video frames of the second spectrum.

Optionally, identifying the first region of interest corresponding to the first feature of the target tissue comprises identifying the first feature of the target tissue by image analysis of one or more frames of the first series of video frames.

Optionally, identifying the first region of interest corresponding to the first feature of the target tissue comprises receiving a user input specifying the first region of interest.

Optionally, receiving the user input specifying the first region of interest comprises determining a location on a display at which the image capture device is aimed, wherein the location on the display is displaying the first region of interest at a time at which the image capture device is aimed at the location on the display.

Optionally, the first spectrum is a visible light spectrum.

Optionally, the second spectrum is a NIR infrared spectrum.

According to an aspect, a computer program product including computer implementable instructions, or a non-transitory computer-readable storage medium for medical video analysis is provided, the non-transitory computer-readable storage medium storing instructions. The instructions are configured to be executed by one or more processors of a medical video analysis system comprising an image capture device configured to detect white light and infrared light and a display assembly configured to display one or more images captured by the handheld device, wherein executing the instructions causes the system to: capture a first series of video frames of target tissue in a first spectrum; capture a second series of video frames of the target tissue in a second spectrum, wherein the second series of video frames is captured simultaneously with capturing of the first series of video frames; identify a first region of interest in one or more frames of the first series of video frames, the first region of interest corresponding to a first feature of the target tissue; apply a tracking algorithm to track the first feature of the target tissue in the first series of video frames, wherein the tracking algorithm is configured to track the first feature of the target tissue independently from tracking of surrounding tissue; and identify a second region of interest in one or more frames of the second series of video frames based on the tracking algorithm applied to the first series of video frames, the second region of interest corresponding to the first feature of the target tissue.

According to an aspect, a medical video analysis method is provided, the method performed at a medical video analysis system comprising an image capture device configured to detect white light and infrared light, a display assembly configured to display one or more images captured by the handheld device, and one or more processors, the method comprising: capturing a first series of video frames of target tissue in a first spectrum; capturing a second series of video frames of the target tissue in a second spectrum, wherein the second series of video frames is captured simultaneously with capturing of the first series of video frames; identifying a first region of interest in one or more frames of the first series of video frames, the first region of interest corresponding to a first feature of the target tissue; applying a tracking algorithm to track the first feature of the target tissue in the first series of video frames, wherein the tracking algorithm is configured to track the first feature of the target tissue independently from tracking of surrounding tissue; and identifying a second region of interest in one or more frames of the second series of video frames based on the tracking algorithm applied to the first series of video frames, the second region of interest corresponding to the first feature of the target tissue.

According to an aspect, an image capture and display system for tissue sample tracking, comprising: a handheld image capture and pointing device; a display assembly configured to display one or more images captured by the handheld device; and one or more processors configured to cause the system to: capture, by the image capture and pointing device, an image; display, by a display of the display assembly, the image; while the image is displayed by the display, determine a location on the display assembly at which the handheld device is aimed, wherein the location on the display corresponds to a region in the displayed image, wherein the region in the displayed image comprises a target tissue area; and in response to detecting a user input and determining the location on the display assembly, generate and store annotation data associated with the target tissue area.

Optionally, the annotation data comprises data indicating a region of interest in the image.

Optionally, the annotation data comprises a label for the target tissue area generated based on the user input.

Optionally, the annotation data comprises time-stamp data generated based on a time-stamp of the image displayed on the display assembly.

Optionally, the annotation data comprises a unique identifier automatically generated by the system.

Optionally, the annotation data is stored in association with a tissue sample taken from the target tissue area.

Optionally, the annotation data is stored in association with pathology results data associated with the tissue sample taken from the target tissue area.

Optionally: the image is captured by the image capture and pointing device, as part of a first time series of video frames of the target tissue in a first spectrum; and the one or more processors cause the system to: capture, by the image capture and pointing device, a second time series of video frames of the target tissue in a second spectrum; and in response to detecting a user input and in accordance with the determined location on the display assembly, identify a region of interest in one or more frames of the second series of video frames and apply an image analysis algorithm to the region of interest in the one or more frames of the second series of video frames.

According to an aspect, a non-transitory computer-readable storage medium for image capture and display for tissue sample tracking is provided, the non-transitory computer-readable storage medium storing instructions configured to be executed by one or more processors of a system for image capture and display for tissue sample tracking comprising a handheld image capture and pointing device and a display assembly configured to display one or more images captured by the handheld device, wherein executing the instructions causes the system to: capture, by the image capture and pointing device, an image; display, by a display of the display assembly, the image; while the image is displayed by the display, determine a location on the display assembly at which the handheld device is aimed, wherein the location on the display corresponds to a region in the displayed image, wherein the region in the displayed image comprises a target tissue area; and in response to detecting a user input and determining the location on the display assembly, generate and store annotation data associated with the target tissue area.

According to an aspect, a method for image capture and display for tissue sample tracking is provided, the method performed at a system for image capture and display for tissue sample tracking comprising a handheld image capture and pointing device, a display assembly configured to display one or more images captured by the handheld device, and one or more processors, the method comprising: capturing, by the image capture and pointing device, an image; displaying, by a display of the display assembly, the image; while the image is displayed by the display, determining a location on the display assembly at which the handheld device is aimed, wherein the location on the display corresponds to a region in the displayed image, wherein the region in the displayed image comprises a target tissue area; and in response to detecting a user input and determining the location on the display assembly, generating and storing annotation data associated with the target tissue area.

Examples of the methods disclosed herein can be used for non-invasive imaging of tissue of the patient. The imaged tissue can be external tissue of the patient, such as skin. Alternatively, the imaged tissue can be tissue underneath the skin imaged through the intact skin. Alternatively, the imaged tissue can be pre-exposed tissue inside the patient. Some examples of the methods disclosed herein do not encompass the step of exposing internal tissue of the patient.

It will be appreciated that any of the aspects, features and options described in view of the system(s) apply equally to the method(s), computer program product and computer-readable storage medium(s), and vice versa. It will also be clear that any one or more of the above aspects, features and options can be combined. According to an aspect, any one or more of the characteristics of any one or more of the systems, methods, and/or computer-readable storage mediums recited above may be combined, in whole or in part, with one another and/or with any other features or characteristics described elsewhere herein.

BRIEF DESCRIPTION OF THE FIGURES

The patent or application file contains at least one drawing executed in color. Copies of this patent or patent application publication with color drawing(s) will be provided by the Office upon request and payment of the necessary fee.

Features will become apparent to those of ordinary skill in the art by describing in detail exemplary aspects with reference to the attached drawings in which.

DETAILED DESCRIPTION

Figure 1:
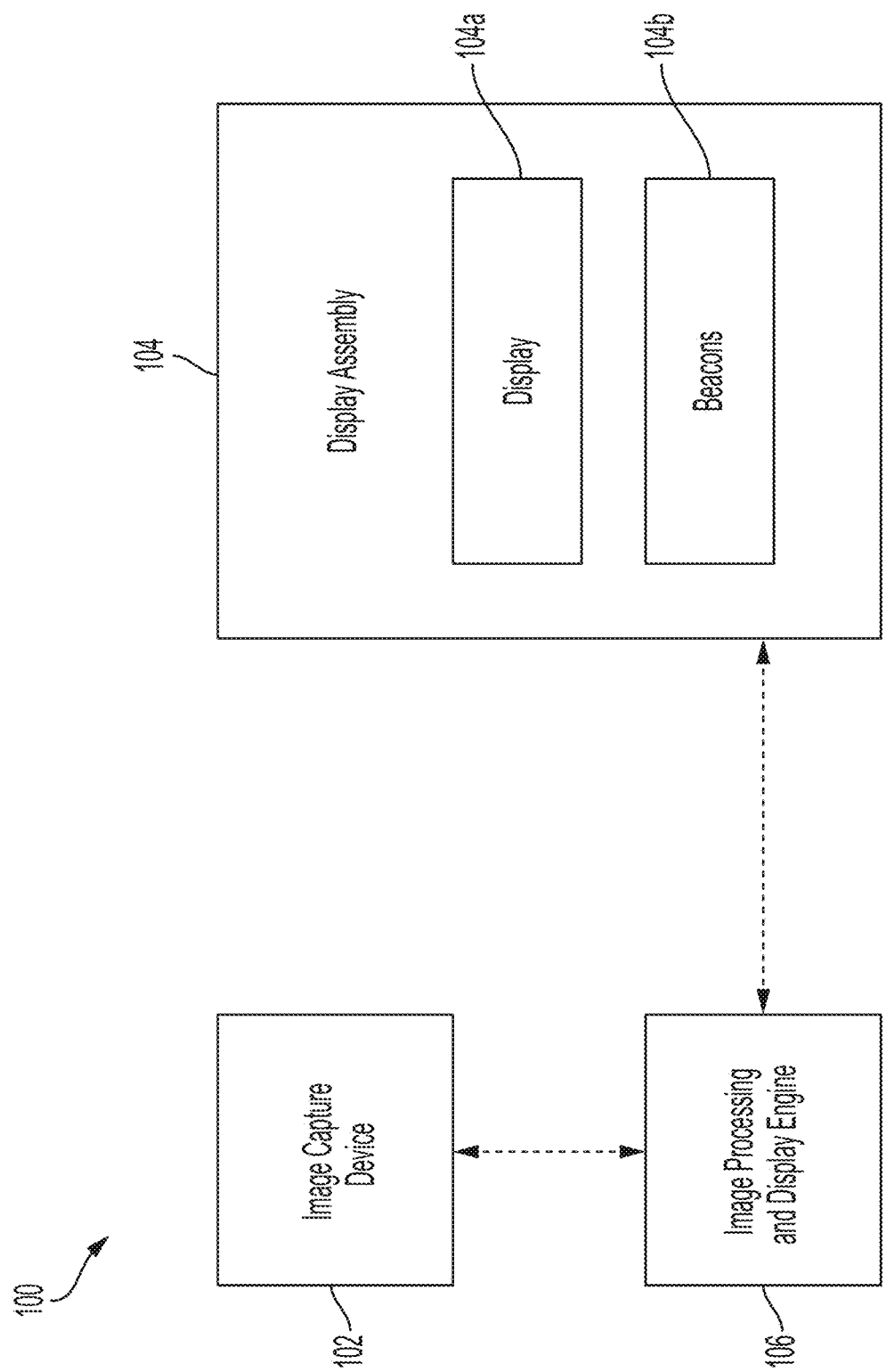
FIG. 1 depicts a system for medical image medical image capture, display, manipulation, annotation, and analysis, in accordance with some aspects.
Figure 2:
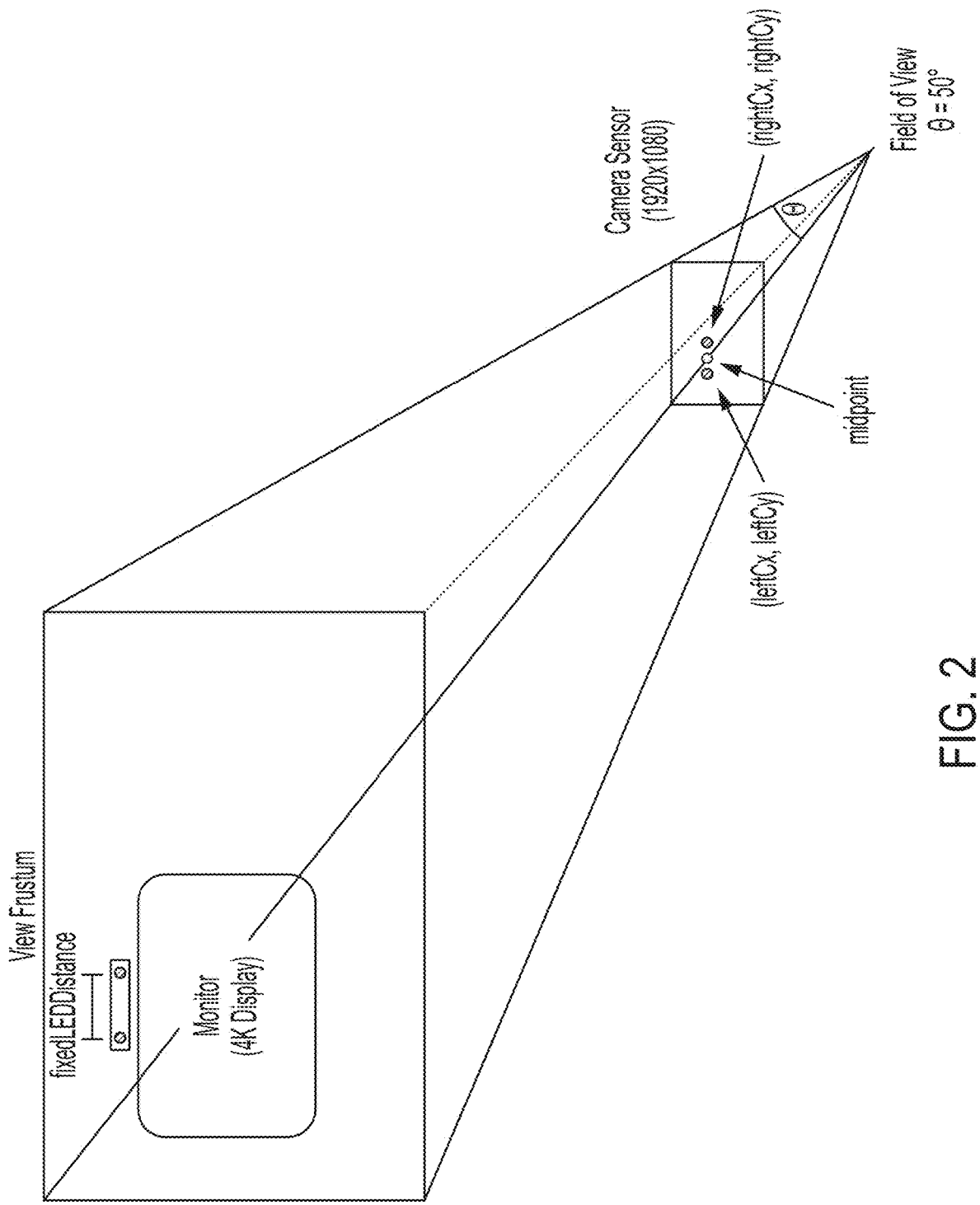
FIG. 2 depicts a view frustum of an image capture device, in accordance with some aspects.

Reference will now be made in detail to implementations and aspects of various aspects and variations of systems and methods described herein. Although several exemplary variations of the systems and methods are described herein, other variations of the systems and methods may include aspects of the systems and methods described herein combined in any suitable manner having combinations of all or some of the aspects described.

As explained in detail below, this disclosure sets forth systems, methods, and techniques for medical image/video capture, medical image display, medical image control and manipulation, medical image/video annotation, and/or feature tracking in medical images/videos.

As explained below, the techniques set out herein may enable capturing, displaying, and manipulating medical images and videos. A handheld image capture and pointing device may include one or more image sensors configured to capture both white light video/images and infrared video/images. (As used herein, "infrared" or "IR" may refer to infrared and/or near-infrared ("NIR") light.) The handheld image capture and pointing device may be aimed at a region of tissue of a patient and the one or more image sensors may capture a series of video frames in white light and a series of video frames in infrared light. An image from one of the captured video frames may be displayed on a display of a display assembly, wherein the display assembly comprises one or more infrared beacons positioned proximate to the display assembly and configured to emit infrared light. After capturing the image with the handheld device, and while the image is displayed on the display assembly, the operator may aim the handheld device at the display assembly such that the infrared beacons are within the field of vision of the handheld device and such that the infrared light emitted by the beacons is detected by one or more of the image sensors of the device. Based on the infrared light detected by the device, a processor associated with the system may determine a position and/or orientation of the handheld device relative to the display assembly, and the system may cause a graphical user interface including the displayed image to be updated in accordance with the determined position and/or orientation. For example, the graphical user interface may be updated by annotating the displayed image, zooming the displayed image or scaling the size of an annotation on the image, rotating the displayed image or an annotation on the image, or the like. Thus, the user of the handheld image capture and pointing device may be able to use a single device both to capture medical images and to manipulate the images while they are displayed, obviating the need to frequently switch between different devices during medical procedures.

As also explained below, the techniques set out herein may enable using frame-synchronized object tracking to identify regions of medical video streams for analysis and/or visualization. A system for medical image capture, display, manipulation, annotation, and analysis may be configured such that two (or more) video streams depicting the same target tissue may be simultaneously captured, wherein a first one of the video streams captures the target tissue in a first spectrum (e.g., white light) and a second one of the video streams captures the target tissue in a second spectrum (e.g., IR). An object such as a tissue feature may be tracked in one video stream (e.g., a white light video stream) to determine a region of the other video stream (e.g., an IR video stream) at which image analysis should be performed or from which data should be extracted. In this manner, a system may be configured to use frame-synchronized video channels (e.g., video streams) to extract information out of a first channel of video (e.g., a white light video channel) and apply that information to corresponding positions in the second channel of video (e.g., an IR video channel).

As also explained below, the techniques set out herein may enable capturing medical images and generating annotation data to be stored in association with a region of interest in the medical image and/or in association with a tissue sample extracted from the tissue at an area indicated by the region of interest in the image. A system may capture a medical image (e.g., a frame from a medical video) using a handheld image capture and pointing device, display said medical image on a display assembly, determine a location in said image displayed on said display assembly at which the handheld device is pointed, and generate and store annotation data associated with a region of interest defined in the image at the location at which the handheld device is pointed.

While the disclosure herein is set forth using examples regarding capturing, displaying, manipulating, annotating, and analyzing medical images and videos, a person of ordinary skill in the art would recognize that the disclosure herein may be similarly applied to other fields of endeavor to capture, display, manipulate, annotate, and analyze images and videos that are not medical images or medical videos.

Figure 12:
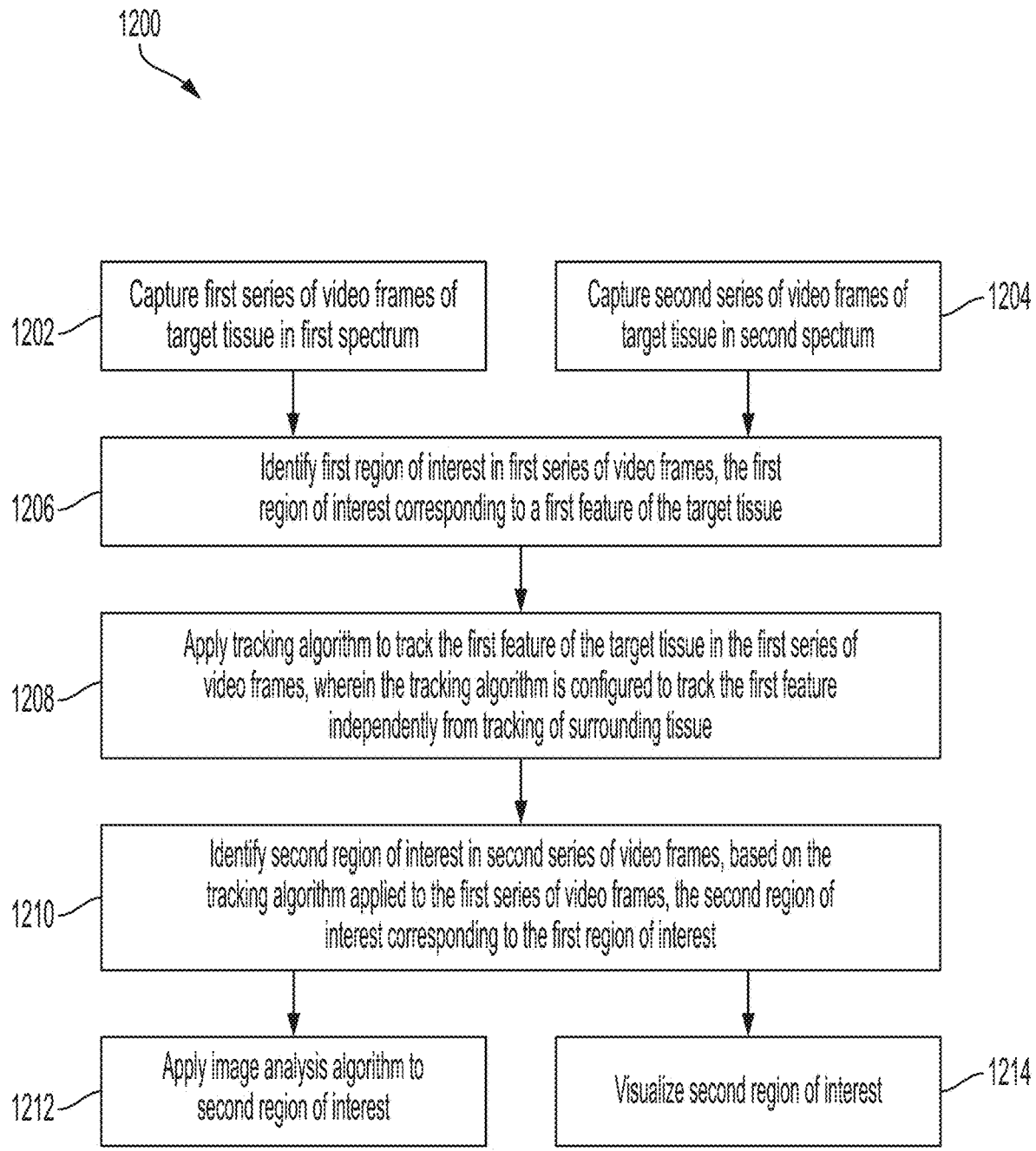
FIG. 12 depicts a method of capturing medical video and identifying regions of interest therein, in accordance with some aspects.
Figure 13:
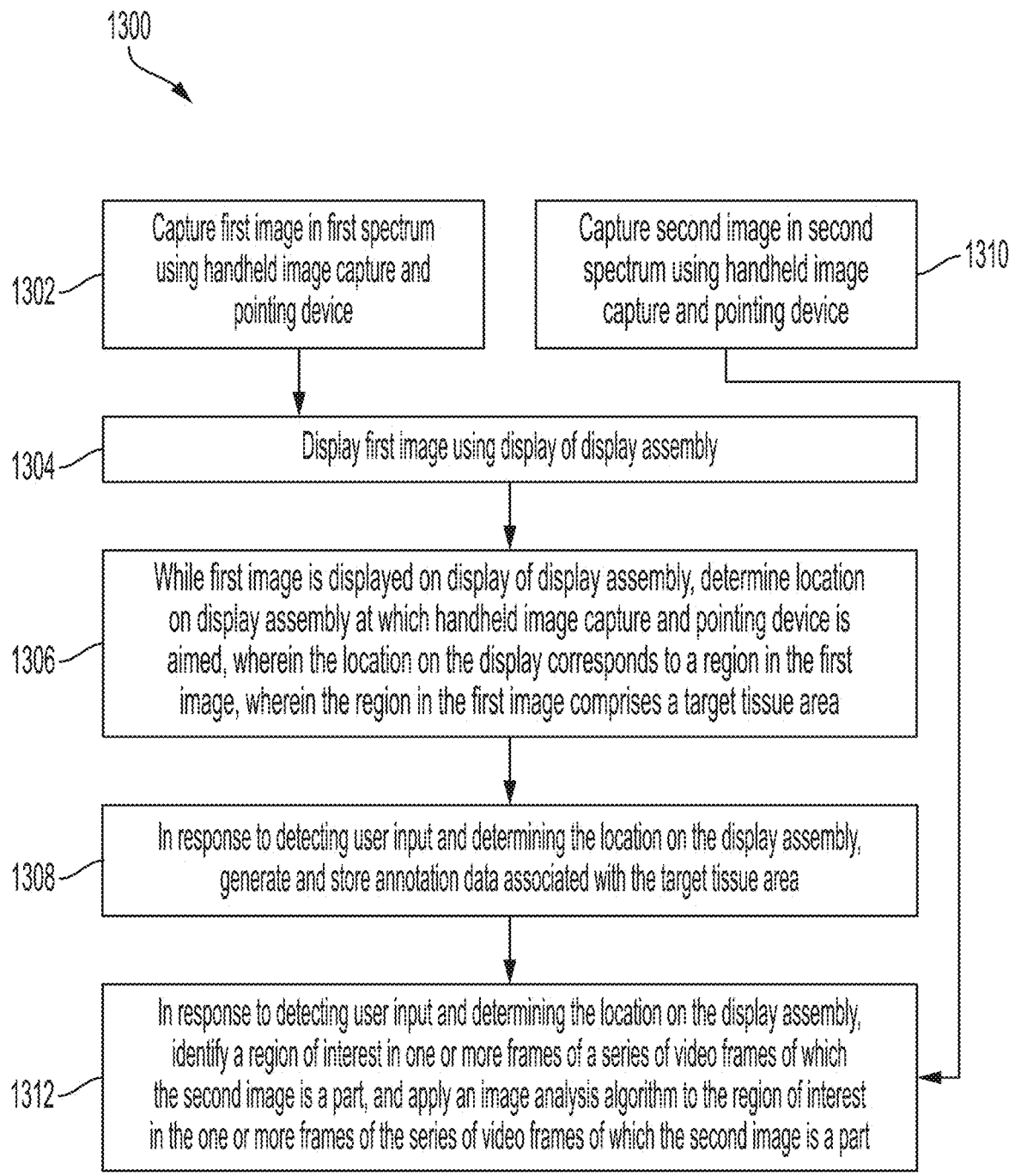
FIG. 13 depicts a method of capturing medical images and annotating said medical images using a handheld medical image capture and pointing device, in accordance with some aspects.
Figure 14:
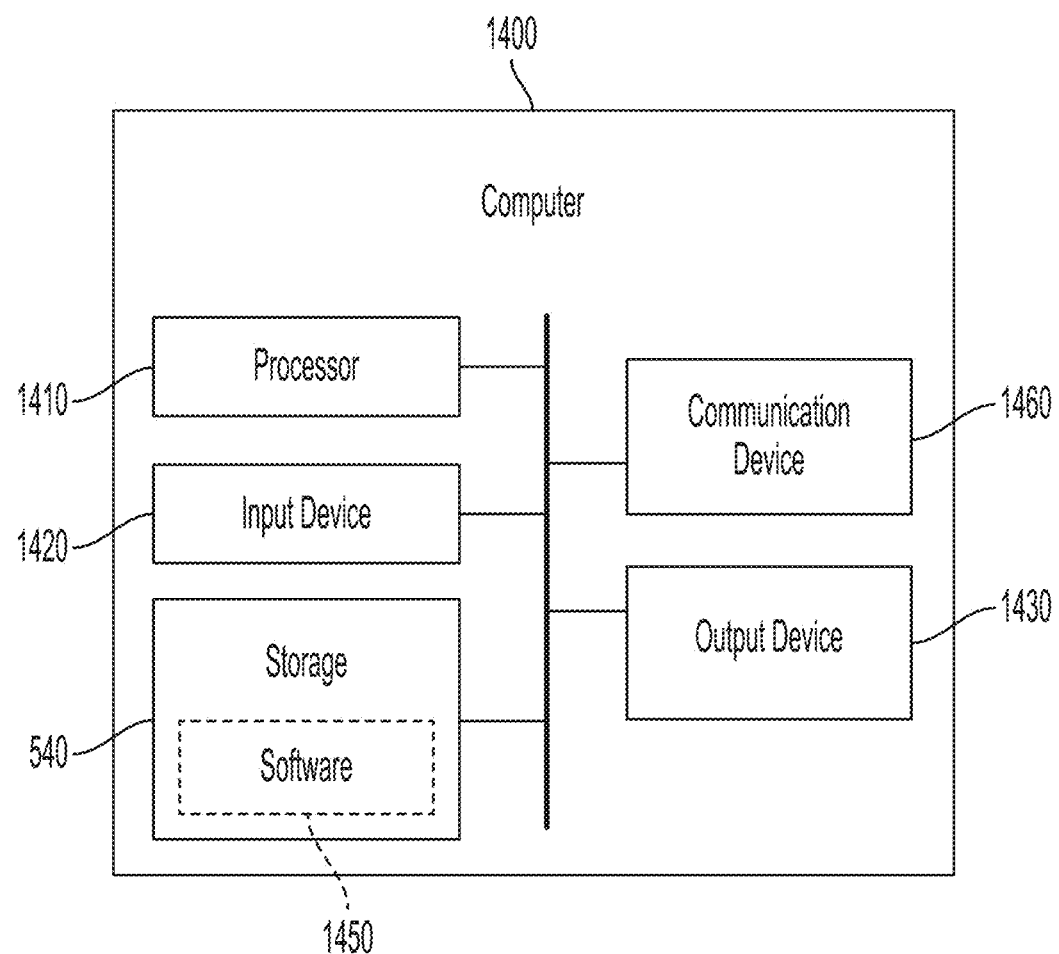
FIG. 14 depicts a computer, in accordance with some aspects.

Below, FIG. 1 and the accompanying description describe an exemplary system for medical image capture, display, manipulation, annotation, and analysis; FIGS. 2-11 and the accompanying description describe exemplary techniques for capturing a medical image using a handheld device and controlling a graphical user interface comprising the captured image based on a determined position and/or determined orientation of the handheld device with respect to a display assembly on which the graphical user interface is displayed; FIG. 12 and the accompanying description describe exemplary techniques for simultaneously capturing multiple medical image video streams in multiple different spectra and identifying a region of interest in frames of one of the video streams based on a tracking algorithm applied to the other video stream; FIG. 13 and the accompanying description describes techniques for capturing a medical image using a handheld device and generating annotation data in the image based on a determined position and/or determined orientation of the handheld device with respect to a display assembly on which the captured image is displayed; and FIG. 14 depicts an exemplary computer that may be used to execute all or part of any one or more of the techniques described herein.

Exemplary System

FIG. 1 depicts a system 100 for medical image capture, display, manipulation, annotation, and analysis, in accordance with an example. As shown, system 100 may include image capture device 102, image processing and display engine 106, and display assembly 104. Each of these components may be communicatively coupled with one or more of the other components such that they may send and receive electronic information via network communication amongst one another. For example, as shown by the dotted lines in FIG. 1, engine 106 may be communicatively coupled with each of image capture device 102 and display assembly 104.

In this example, image capture device 102 may be any device comprising one or more image sensors and configured to capture one or more medical images and/or videos. The image capture device 102 may comprise multiple image sensors each configured to capture images/video in different spectra, for example a white light image sensor and an infrared image sensor disposed proximate to one another and oriented in essentially the same direction so as to be able to simultaneously capture images/video in different spectra of the same tissue area. Image capture device 102 may comprise a single image sensor configured to detect light across a plurality of different spectra, and one or more processors associated with image capture device 102 may be configured to process signals from the single image sensor to generate captured images and/or video in multiple different spectra based on the light captured by the single image sensor.

In this example, image capture device 102 is a handheld image capture device configured to be held in the hand of a medical practitioner such as a surgeon during use. Device 102 may be sufficiently small and lightweight to be able to be held and moved and aimed in one hand by a user. A medical practitioner using device 102 may be able to aim device 102 by hand at a tissue area of a patient in order to capture video and/or images or the patient's tissue. The device 102 may comprise one or more buttons, triggers, or other input devices that may be activated by a user in order to cause device 102 to capture a still image and/or to start or stop recording video.

Here, image capture device 102 is communicatively coupled to one or more other devices and/or systems, such as other components of system 100 including image processing and display engine 106, by any wired or wireless electronic communication medium, including by any suitable network communication protocol. Image capture device 102 may be configured to transmit captured image data (e.g., medical/surgical image data and/or medical/surgical video data), associated metadata, and/or other data to image processing and display engine 106.

In this example, display assembly 104 is a device configured to display one or more images and/or video captured by image capture device 102 on a display 104a of display assembly 104. Here, display assembly 104 may be communicatively coupled to one or more other devices and/or systems, such as other components of system 100 including image processing and display engine 106, by any wired or wireless electronic communication medium, including by any suitable network communication protocol. Display assembly 104 may be configured to receive image data (e.g., medical/surgical image data and/or medical/surgical video data), associated metadata, and/or other data from image processing and display engine 106 and use said received data to render one or more GUIs including captured images/video on display 104a or display assembly 104.

In addition to display 104a, display assembly 104 may comprise beacons 104b, which may include one or more beacons positioned proximate to display 104a and configured to allow system 100 to determine a position and/or orientation of device 102 with respect to display assembly 104, as discussed in detail hereinbelow. Beacons 104b may comprise one or more fixed objects configured to be visually detectible by an image sensor of device 102 to be used to allow system 100 to determine a position and/or orientation of device 102 with respect to display assembly 104. Beacons 104b may comprise physical objects visible in white light, infrared light, or one or more other spectra; virtual beacons displayed on display 104a; and/or dedicated light-emitting elements positioned proximate to display 104 and configured to emit light visible in white light, infrared light, or one or more other spectra.

Image processing and display engine 106 may be any device or system comprising one or more computer processors configured (1) to receive image data, associated metadata, and/or other data from image capture device 102, (2) to send processed image data and/or other data directly or indirectly to display assembly 104, and (3) to perform image processing and GUI control operations as explained in detail herein below. Engine 106 may be configured to generate, update, and/or otherwise provide a GUI for display on display assembly 104, including determining a position and/or orientation of device 102 with respect to display assembly 104 and generating, updating, and/or otherwise providing the GUI (including captured images controlled therein) based at least in part on the determined position and/or orientation.

In this example, image capture device 102 may be an image capture and pointing device configured to both capture images/video as described above and to serve as a pointing and control device for pointing at and executing controls against a graphical user interface (GUI) displayed on a display assembly such as display assembly 104. Exemplary techniques by which device 102 may be used to point at and control a GUI displayed on display assembly 104 are described below throughout this disclosure in detail. Device 102 may be used to control a GUI displayed on display assembly 104 and/or to annotate or otherwise manipulate an image displayed as part of a GUI on display assembly 104 wherein the image displayed as part of the GUI is an image that was previously captured by device 102.

In this example, device 102 may be configured to operate selectably in either an image-capture mode for capturing images/video or in a pointer/control mode for pointing at a displayed GUI and/or executing one or more controls against the GUI. Device 102 may be toggled between the two modes based on manual selection by a user (e.g., by a user pressing a button, toggling a switch, or otherwise executing an input). For example, device 102 may be configured to automatically toggle between the two modes, for example based on an automatic detection by the device of whether it is aimed at patient tissue and/or whether it is aimed at a display assembly and GUI. For example, system 100 may automatically determine whether or not device 102 is aimed at a display assembly and GUI using automated image analysis and/or tracking algorithms to analyze images captured by the device; alternatively, or additionally, system 100 may automatically determine whether or not device 102 is aimed at a display assembly and GUI based on detection by one or more sensors of device 102 of light emitted from one or more beacons of a display assembly, as discussed in further detail below. In this example, system 100 may automatically determine whether or not device 102 is aimed at a display assembly and GUI based on information collected from one or more of a compass, accelerometer, and gyroscope on-board device 102.

In this example, for example when device 102 is operating in pointer/control mode, control of a GUI and/or an image displayed therein by device 102 may be based at least in part on a determined orientation of device 102 with respect to display assembly 104 and/or on a determined position of device 102 with respect to display assembly 104. In this manner, device 102 may be used, for example, as a pointer to control movement of a cursor on a GUI displayed on display assembly 104. Various functionalities for controlling a GUI displayed on display 104 based at least in part on determining a location on display assembly 104 at which device 102 is aimed may include, for example, displaying a cursor, selecting a displayed graphical user interface object, highlighting a displayed graphical user interface object, selecting a displayed graphical user interface object, rotating a displayed graphical user interface object, zooming/resizing a displayed graphical user interface object, placing a graphical user interface object, and/or generating and placing an annotation on an image displayed as part of the GUI.

Techniques for determining a location of display assembly 104 at which device 102 is aimed, thereby enabling control of a GUI displayed on assembly 104 by device 102, are explained in detail below with reference to FIGS. 2-10.

Exemplary Image Capture, Display, and Manipulation Techniques

Figure 3B:
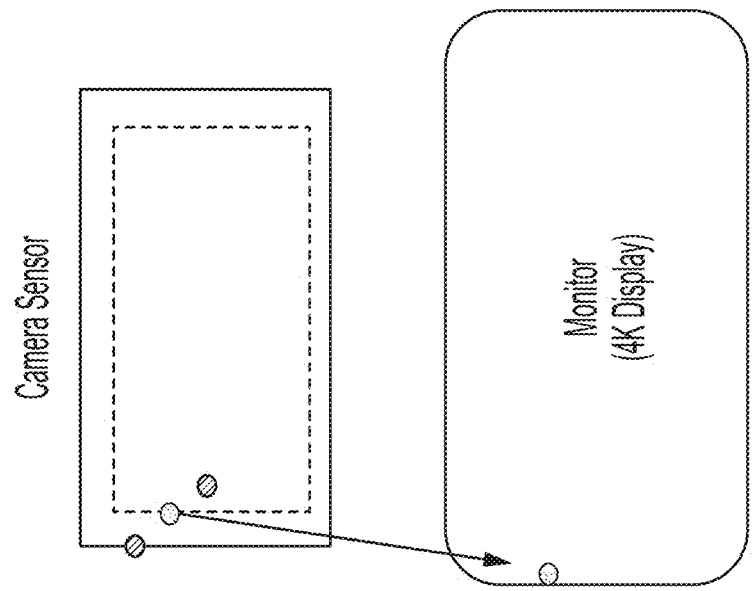
FIGS. 3A and 3B depict configurations of a camera sensor and display of a display assembly, in accordance with some aspects.
Figure 3A:
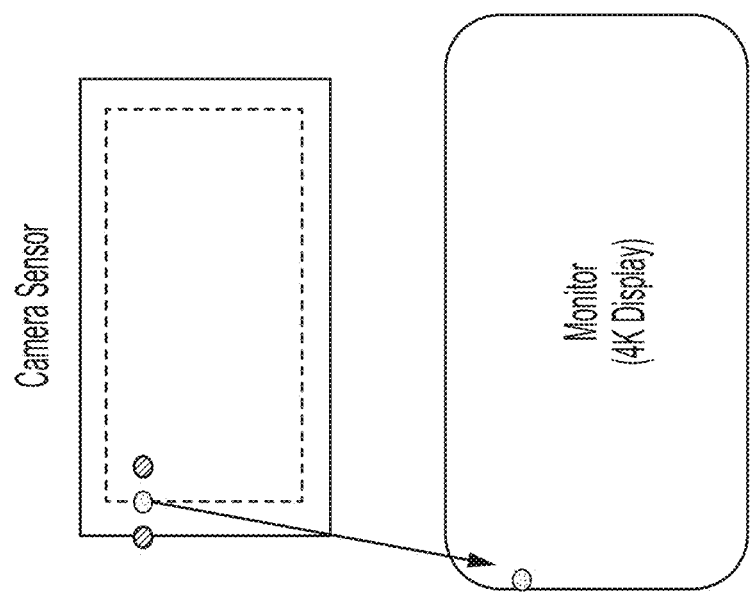
Figure 4B:
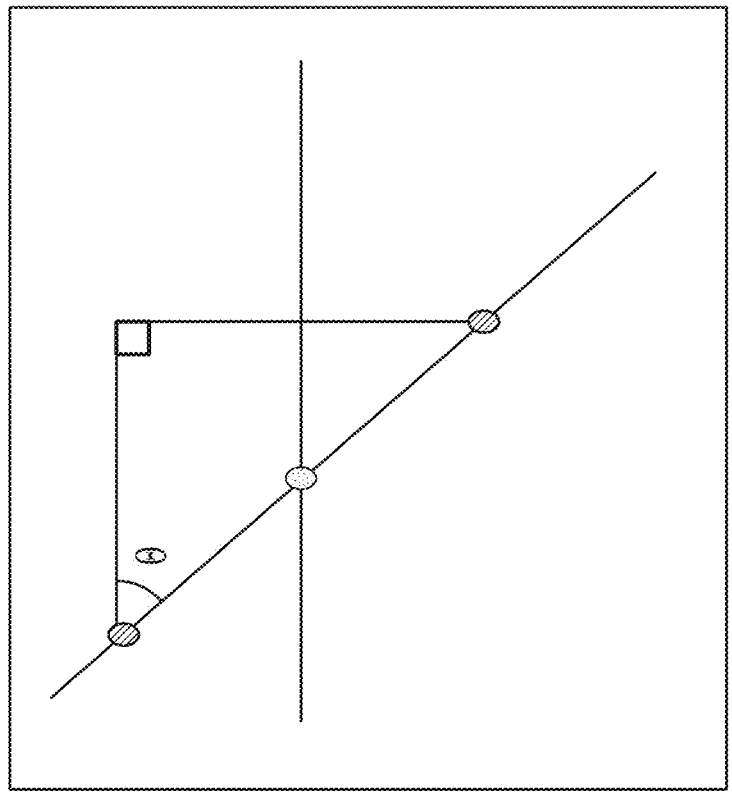
FIGS. 4A and 4B depict configurations of a camera sensor, in accordance with some aspects.
Figure 4A:
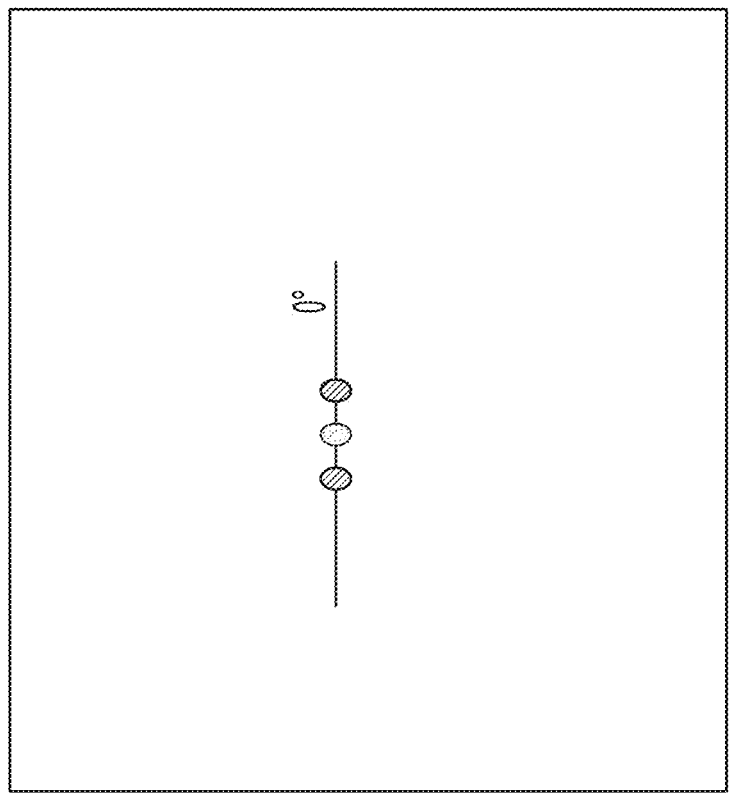

FIGS. 3A & 3B show a location on a display corresponding to the calculated midpoint location and the respective bounding frame dimensions. FIG. 3A depicts an orientation in which the sensor of the handheld device is level with the horizontally-spaced beacons, whereas FIG. 3B depicts an orientation in which the sensor is rotated diagonally with respect to the beacons. In this example, the calculated bounding frame may dynamically change in size as the sensor is rotated, such that the bounding frame may be closer to the edge of the sensor space when the sensor is rotated diagonally (e.g., FIG. 3B) as compared to when the sensor is held on a level horizontal with the beacons (e.g., FIG. 3A). As shown, when the camera is rotated then the midpoint may be slightly closer to the edge of the sensor than if the camera were horizontal.

In this example, the sensor-space inside the dynamically-calculated bounding frame may be mapped to the display space of the physical display. The system may be configured such that the entire sensor space cannot be used, because using the periphery of the sensor space outside the calculated bounding frame would cause the system to lose track of one of the beacons. The system cannot track the midpoint in the sensor space outside of the bounding frame. If the point that is being tracked is on the edge of the calculated bounding frame (e.g., is on the bounding line), then the corresponding position on the physical display (e.g., the calculated cursor position) may be on a corresponding edge of the display space.

The midpoint position in relation to the bounding frame dimensions may be used to calculate a location on the display at which the camera is aimed (e.g., which may be used to determine a position at which a cursor may be rendered on the GUI). For example, for a surgical display that has a resolution of 4K UHD (3840×2160 pixels), then the variables screenWidth and screenHeight may represent these screen pixel dimensions. A proportion may be used to calculate the position of the cursor: the position of midpointX within the boundingFrameWidth may be proportional to the location cursorX within the screenWidth; and the position of midpointY within the boundingFrameHeight may be proportional to the location cursorY within the screenHeight. Cursor position may thus be calculated as follows:

$$\text{cursor}X = (\text{screenWidth} * \text{midpoint}X)/\text{boundingFrameWidth} \quad (1)$$

$$\text{cursor}Y = (\text{screenHeight} * \text{midpoint}Y)/\text{boundingFrameHeight} \quad (2)$$

Beyond calculating a location on the display of a display assembly at which the image capture device is aimed (and therefore at which a cursor may be displayed), the system (e.g., system 100) may be configured to calculate one or more additional properties related to the position and/or orientation of the handheld image capture device relative to the display assembly.

In this example, the system may be configured to calculate camera rotation. Camera rotation may be determined, for example, by drawing a line between the left and right beacon positions and calculating an angle Θ that the line is off the horizontal, as shown for example in FIGS. 4A and 4B and as shown in the following equation:

$$\Theta = \cos^{-1}(\text{abs}(\text{right}Cx - \text{left}Cx)/\text{sensorDistanceBetweenPoints}) \quad (3)$$

In this example, the system may be configured to calculate an actual distance of the image capture device to the display. Said actual distance may be calculated, e.g., as follows.

First, the system may calculate a width of a far clipping plane, which may be calculated as the width of the field-of-view at the far clipping plane. This can be calculated based on the fact that (fixedLEDDistance/fieldOfViewWidth) is proportional to (sensorDistanceBetweenBpints/sensorWidth), as shown below:

$$fieldOfViewWidth = (cameraSensorWidth*fixedLEDDistance)/sensorDistanceBetweenPoints \qquad (4)$$

Figure 5:
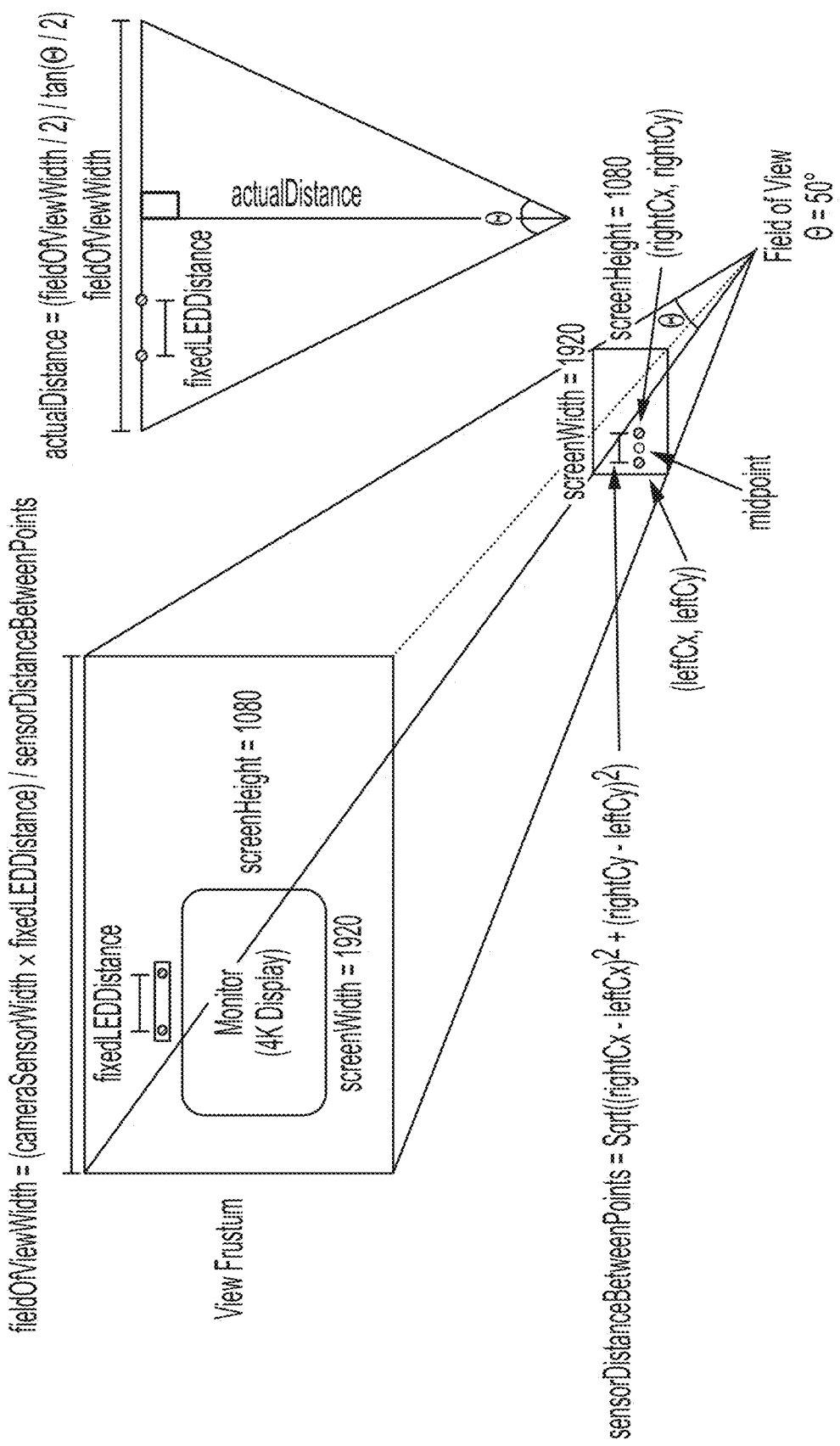
FIG. 5 depicts a diagram of a view frustum of an image capture device and a calculation of distance based thereon, in accordance with some aspects.

Then the system may use the right triangle that is created between the far clipping plane and the camera to calculate the actual distance using the tangent of Θ/2 and solve for the adjacent side of the triangle, as shown in FIG. 5 and by the following equation:

$$actualDistance = (fieldOfViewWidth/2)/\tan(\Theta/2) \qquad (5)$$

The system may be configured to calculate an actual distance of the image capture device to the display in the event that the image capture device is horizontally offset from the center of the screen.

In this example, the system may be configured to automatically determine whether the image capture device is horizontally offset from the display assembly, for example by determining whether one of the left and right IR beacons is larger or smaller on the imaging sensor than the other. Based on whether one or the other of the IR beacons is larger or smaller on the imaging sensor, the system may determine whether the image capture device is horizontally offset and may determine, based on which of the IR beacons is larger or smaller on the imaging sensor, the direction in which the device is offset.

Figure 6B:
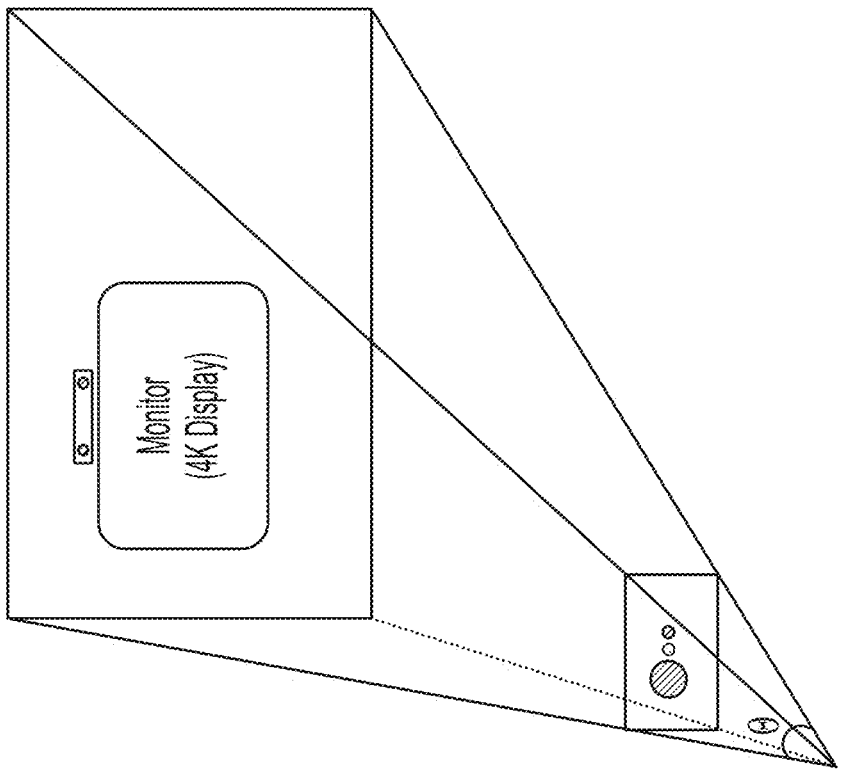
FIGS. 6A and 6B depicts two view frustums of an image capture device in which the image capture device is horizontally offset from a center of the display assembly, in accordance with some aspects.
Figure 6A:
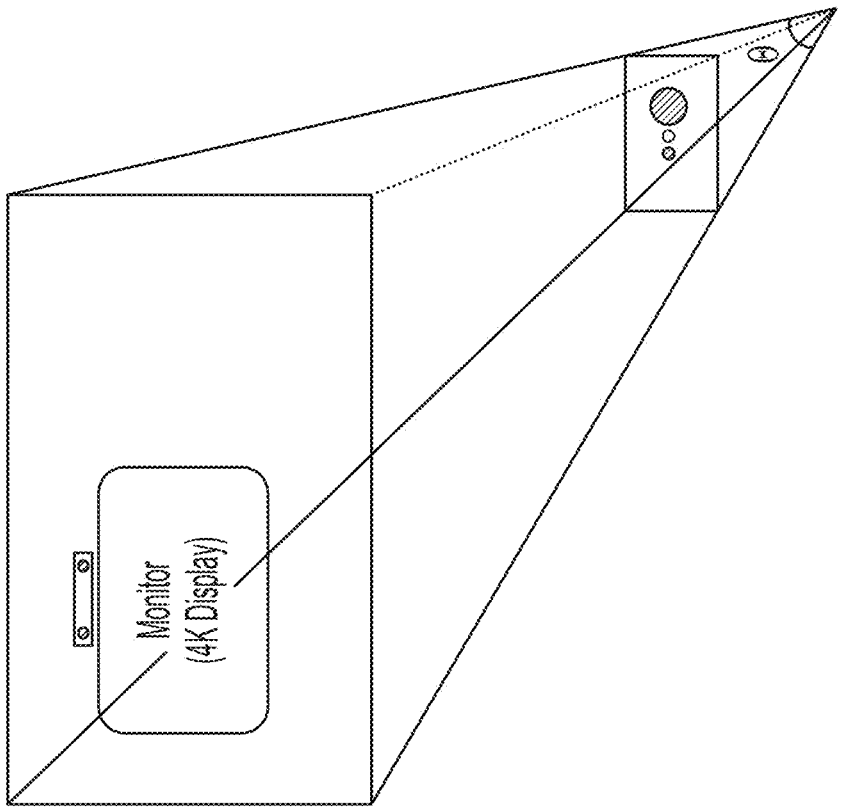

FIGS. 6A and 6B show two examples of the camera sensor being offset from a center of the display assembly. As shown in FIG. 6A, the camera sensor is horizontally offset in a rightward direction from the center of the display assembly, and the right IR beacon, which is closer to the image sensor, therefore appears larger on the image sensor than the left IR beacon. As shown in FIG. 6B, the camera sensor is horizontally offset in a leftward direction from the center of the display assembly, and the left IR beacon, which is closer to the image sensor, therefore appears larger on the image sensor than the right IR beacon.

Figure 7B:
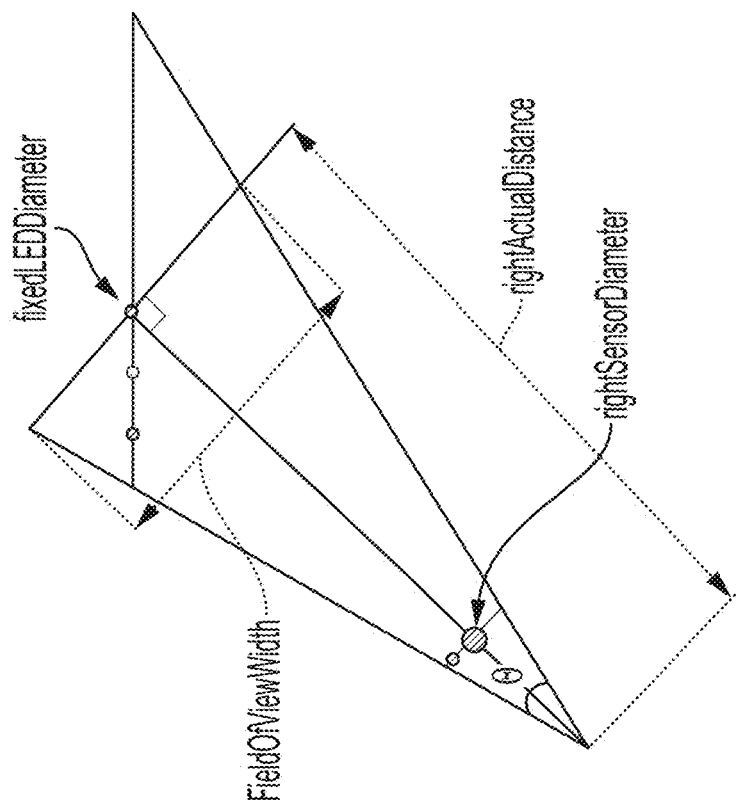
FIGS. 7A and 7B depicts a calculation of distances from an image capture device to beacons of a display assembly in an arrangement in which the image capture device is horizontally offset from a center of the display assembly, in accordance with some aspects.
Figure 7A:
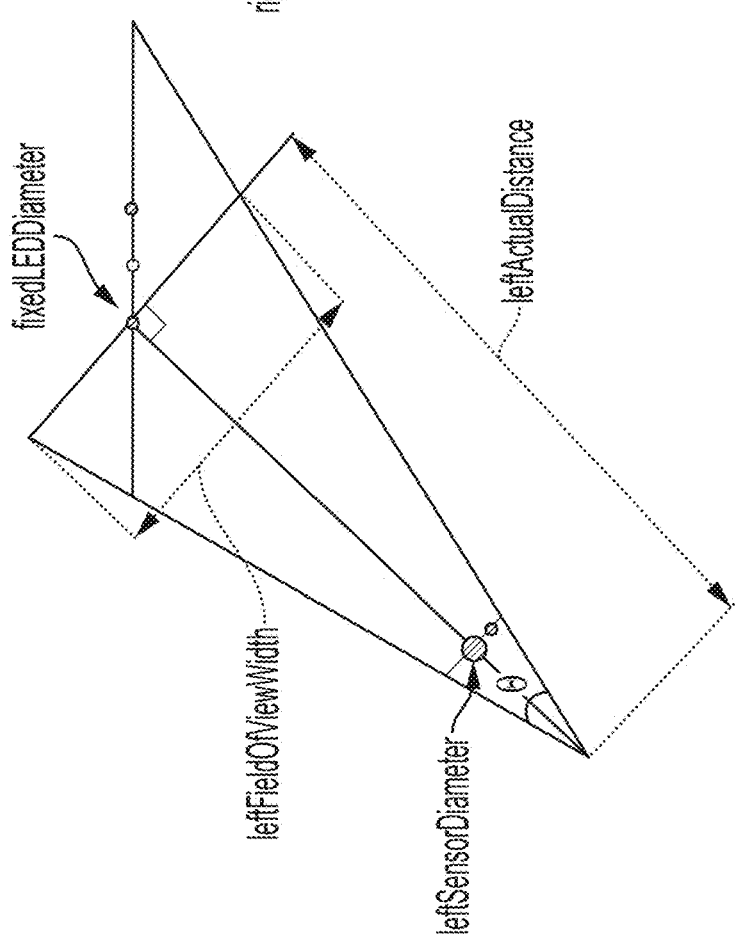

The actual diameter of the IR beacon is fixed (fixedLEDDiameter) and may be known to the system. Thus, the proportion of the fixed diameter on the far clipping plane as compared to the diameter on the sensor may be used to calculate the field-of-view width. Once the field-of-view width is known, then the system can use the tangent of the right triangle to calculate the actual distance from the camera to the left beacon and the actual distance from the camera to right beacon, as shown in FIGS. 7A and 7B and as shown by the following equations:

$$leftFieldOfViewWidth = (sensorWidth*fixedLEDDiameter)/leftSensorDiameter \qquad (6)$$

$$leftActualDistance = (fieldOfViewWidth/2)/\tan(\Theta/2) \qquad (7)$$

$$rightFieldOfViewWidth = (sensorWidth*fixedLEDDiameter)/rightSensorDiameter \qquad (8)$$

$$rightActualDistance = (fieldOfViewWidth/2)/\tan(\Theta/2) \qquad (9)$$

Figure 8:
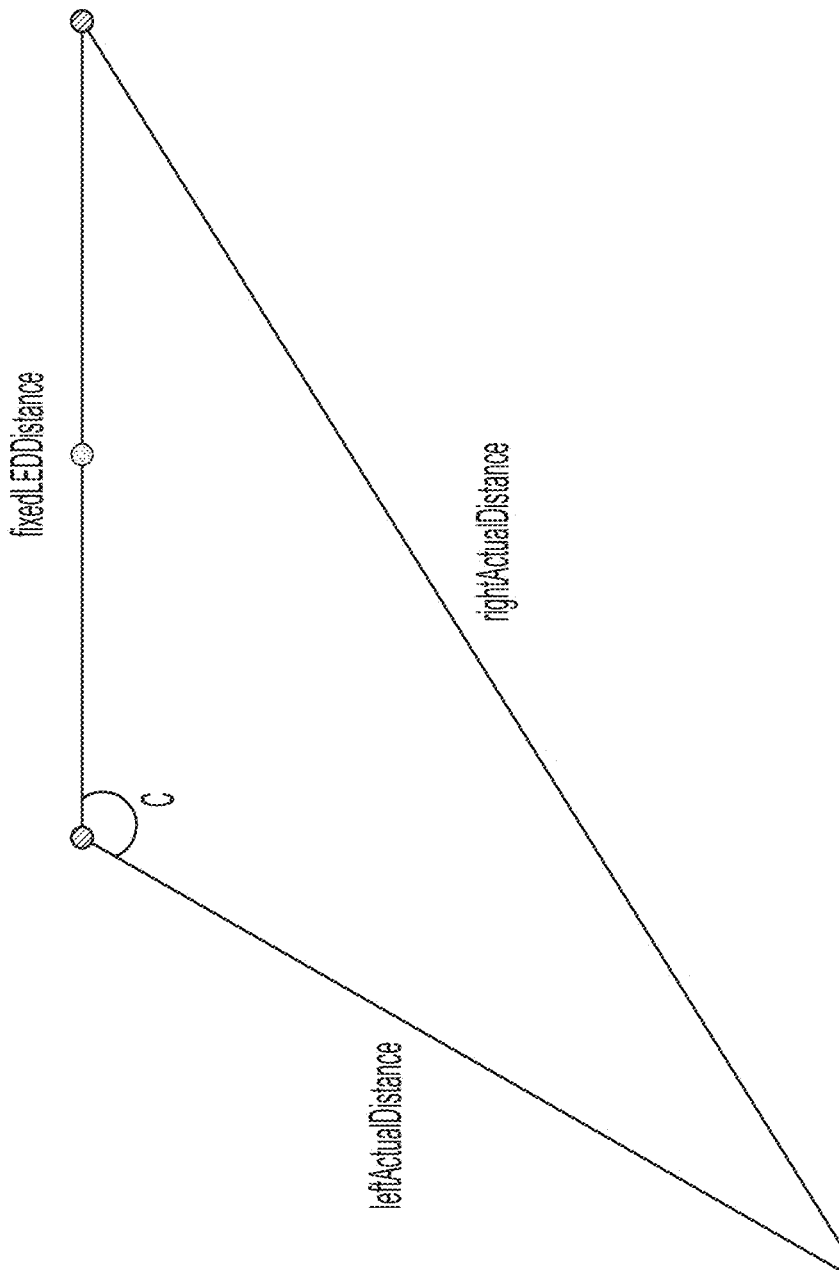
FIG. 8 depicts a calculation of distance, in accordance with some aspects.

Once leftActualDistance and rightActualDistance have been calculated, the system may then use the Law of Cosines ($c^2 = a^2 + b^2 - 2(a)(b)(\cos(C))$) to calculate the unknown angle C, as shown in FIG. 8 and as shown by the following equations:

$$rightActualDistance^2 = fixedLEDDistance^2 + leftActualDistance^2 - 2(fixedLEDDistance)(leftActualDistance)(\cos C) \qquad (10)$$

$$\cos C = (fixedLEDDistance^2 + leftActualDistance^2 - rightActualDistance^2)/(2(fixedLEDDistance)(leftActualDistance)) \qquad (11)$$

Figure 9:
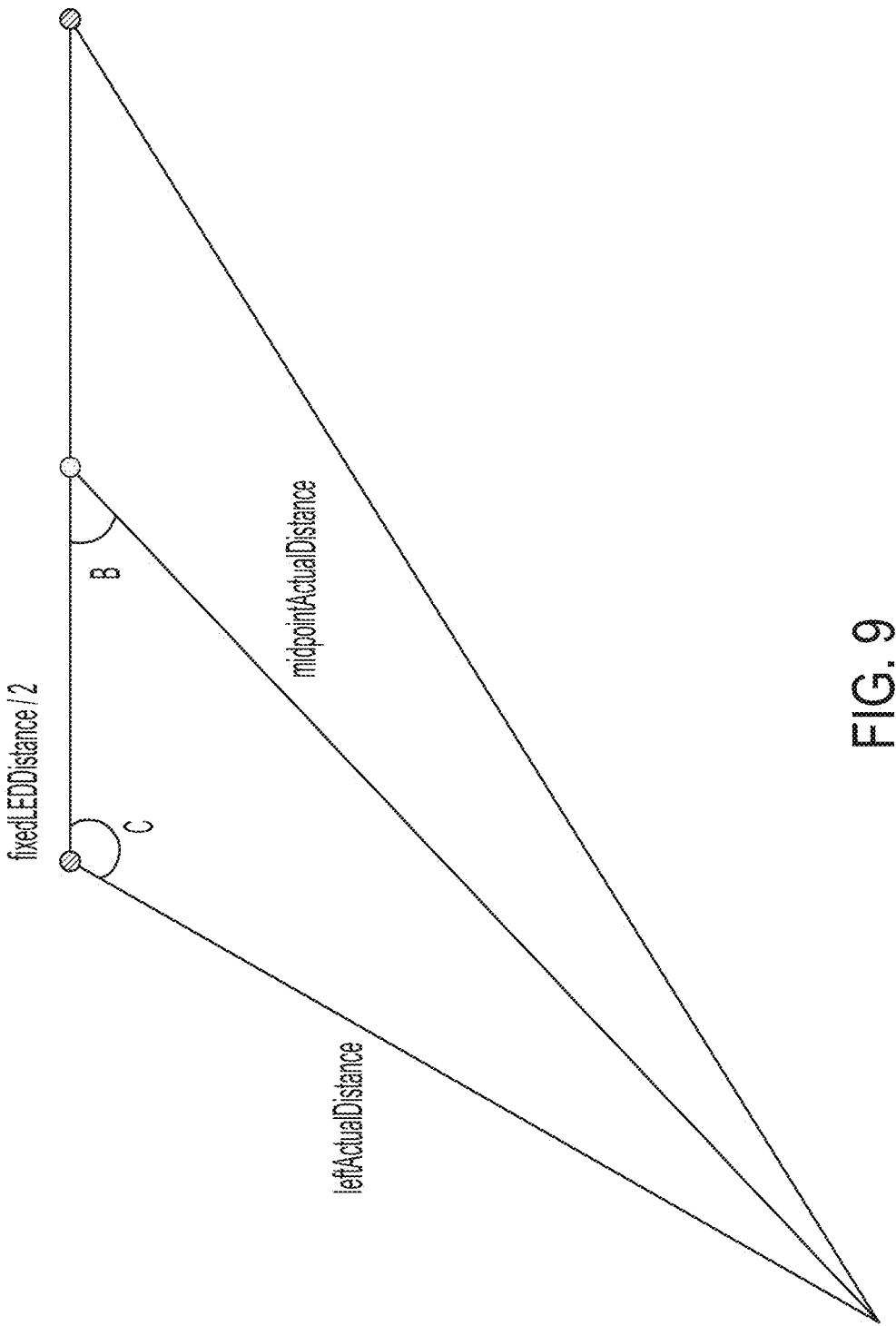
FIG. 9 depicts a calculation of midpoint distance, in accordance with some aspects.

Once the angle C is determined, the system may then apply the law of cosines again to calculate the actual midpoint distance, as shown in FIG. 9 and as shown by the following equations:

$$midpointActualDistance^2 = (fixedLEDDistance/2)^2 + leftActualDistance^2 - 2(fixedLEDDistance/2)(leftActualDistance)(\cos C) \qquad (12)$$

$$midpointActualDistance = \sqrt{((fixedLEDDistance/2)^2 + leftActualDistance^2 - 2(fixedLEDDistance/2)(leftActualDistance)(\cos C))} \qquad (13)$$

Once the angle C and the actual midpoint distance are known, the system may then use the law of cosines once again to solve for angle B, where angle B is the angle that the camera is horizontally offset. This calculation is shown by the following equations:

$$leftActualDistance^2 = midpointActualDistance^2 + (fixedLEDDistance/2)^2 - 2(midpointActualDistance)(fixedLEDDistance/2)(\cos B) \qquad (14)$$

$$\cos B = (midpointActualDistance^2 + (fixedLEDDistance/2)^2 - 2leftActualDistance^2)/(2(midpointActualDistance)(fixedLEDDistance/2)) \qquad (15)$$

$$B = \cos^{-1}((midpointActualDistance^2 + (fixedLEDDistance/2)^2 - 2leftActualDistance^2)/(2(midpointActualDistance)(fixedLEDDistance/2))) \qquad (16)$$

While the above explains techniques in which two horizontally-offset IR beacons are used, other beacon arrangements may be used; for example, a single beacon may be used, three (or more) beacons in a line may be used, three beacons in a triangle may be used, and/or four beacons in a rectangle may be used.

While the above explains techniques by which visual detection of one or more beacons may be used to determine a position and/or orientation of an image capture device, position and/or orientation of an image capture device may also be determined based in whole or in part on data collected from one or more of an accelerometer, a gyroscope, and a compass on board the image capture device. Additionally or alternatively, position and/or orientation of an image capture device may also be determined based in whole or in part on other image processing methods (aside from detection of beacons as explained above), for example by using video tracking and/or applying sparse and/or dense optical flow tracking algorithms to track movement of an image capture device based on video frames captured by the image capture device.

Figure 10:
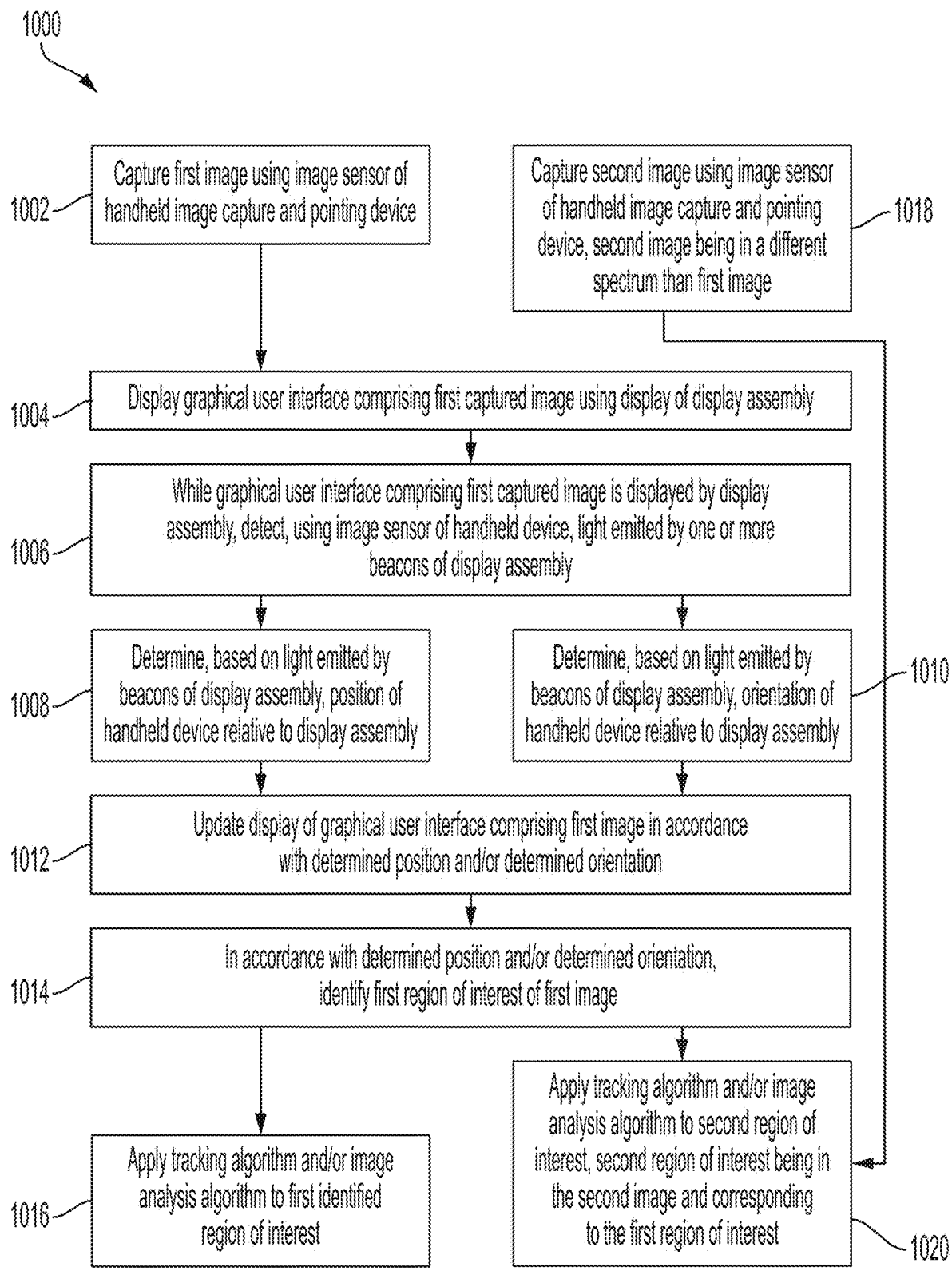
FIG. 10 depicts a method for capturing a medical image and displaying a graphical user interface comprising the captured image, in accordance with some aspects.

FIG. 10 depicts a flowchart representing an exemplary method 1000 for capturing a medical image and displaying a graphical user interface comprising the captured image, in accordance with some aspects.

As described below in detail, method 1000 may enable an image capture and display system to capture medical images using a handheld image capture and pointing device; to display one or more of the captured images on a display assembly as part of a GUI; to calculate a position and/or orientation of the image capture and pointing device relative to the display assembly; and to then control display of the GUI including the captured image based at least in part on the determined relative position and/or orientation.

The method 1000 may be carried out, in whole or in part, by one or more of the components of a system for medical image capture, display, manipulation, annotation, and analysis, such as system 100 described above with respect to FIG. 1. Any one or more of the aspects of method 1000 may be combined, in whole or in part, with any one or more of the aspects of FIG. 1, and/or with any one or more of the systems, methods, devices, and/or techniques described elsewhere herein.

At block 1002, in this example, the system may capture a first image using an image sensor of a handheld image capture and pointing device. In the example of system 100, image capture and pointing device 102 may capture an image of tissue of a patient. The first captured image may be a standalone still image; the first captured image may be a frame of a series of video frames. The first captured image may be an image captured in one or a plurality of spectra in which the image capture device is configured to operate; for example, the captured image may be a white light image.

The first captured image may be processed locally and/or transmitted for remote processing. In the example of FIG. 1, the first captured image may be transmitted (by wired or wireless network communication) to image processing and display engine 106 (where it may be processed and/or caused to be displayed by display assembly 104).

At block 1004, in this example, the system may display a graphical user interface comprising the first captured image using a display of a display assembly. In the example of system 100, image processing and display engine 106 may receive the first captured image from device 102, may optionally process the received first image, and may generate or otherwise provide a graphical user interface comprising the first captured image for display on display 104 by display assembly 104.

In this example, the graphical user interface may be a surgical display graphical user interface configured to allow a surgeon to view raw, processed, and/or annotated surgical images and/or video during a surgical procedure in the surgical environment. As discussed herein, the graphical user interface may be configured to allow a user to annotate one or more displayed images and/or to perform region-of-interest tracking in one or more video streams based on tissue features associated with said annotations.

In this example, the graphical user interface may be configured to allow a user to execute one or more inputs to select, control, manipulate, zoom, rotate, augment, modify, or otherwise control one or more medical images displayed as part of the graphical user interface. The graphical user interface may be configured to be able to be controlled by any suitable input device such as a mouse, keyboard, touchscreen controls, or the like. The graphical user interface may be configured to be able to be controlled by a handheld pointing device, such as image capture and pointing device 102, configured to generate a cursor at a location in the graphical user interface corresponding to a displayed location on the display at which the pointing device is aimed.

At block 1006, in this example, while the graphical user interface comprising the first image is displayed by the display assembly, the system may detect, using an image sensor of the handheld image capture and pointing device, light emitted by one or more beacons of the display assembly. In the example of system 100, image capture device 102 may capture light emitted by one or more of beacons 104b of display assembly 104.

In this example, the beacons may be positioned proximate to a periphery of the display in respective fixed locations relative to the display. As discussed above, the beacons may be configured to emit light in one or more spectra for detection by one or more image sensors of the image capture device 102. Light emitted (and/or reflected) by the one or more beacons may be captured by one or more of the same image sensors used to capture the first image as discussed above with respect to block 1002. Alternatively, or additionally, light emitted (and/or reflected) by the one or more beacons may be captured by one or more of the same image sensors used to capture the second image as discussed below with respect to block 1018. Alternatively, or additionally, light emitted (and/or reflected) by the one or more beacons may be captured by one or more image sensors not used to capture either the first image or the second image.

In this example, one or more of the beacons may be IR beacons. One or more beacons that do not emit light but merely reflect light may be used. One or more virtual beacons generated and displayed on the display displaying the graphical user interface comprising the first image may be used.

Information regarding the detected light emitted from (and/or reflected by) the one or more beacons may be processed locally by the image capture device and/or may be transmitted, for example to an image processing and display engine, for processing remotely.

At block 1008, in this example, the system may determine, based on the light emitted by the one or more beacons of the display assembly, a position of the handheld image capture and pointing device relative to the display assembly. At block 1010 the system may determine, based on the light emitted by the one or more beacons of the display assembly, an orientation of the handheld image capture and pointing device relative to the display assembly. In the example of system 100, the determinations at block 1008 and/or the determination at block 1010 may be made by image processing and display engine 106, and results of said one or more determinations may be used by the image processing and display engine to control one or more aspects of a GUI comprising one or more captured images displayed on display 104.

In this example, determination of a position of a handheld image capture and pointing device relative to a display assembly and/or determination of an orientation of a handheld image capture and pointing device relative to a display assembly may be performed in accordance with all or part of any one or more of the techniques described above with respect to FIGS. 1-9. For example, a system may determine a location at which a handheld pointing device is aimed (e.g., a "cursor position") in a plane of a display assembly, a rotation of a handheld pointing device relative to a display assembly, and/or an actual distance of a handheld pointing device relative to a display assembly. As described below, the system may be configured such that one or more aspects of the displayed GUI including the first captured image displayed therein may be controlled based on the determined position and/or orientation.

In this example, for example as described above with respect to FIGS. 1-9, determining a position of a handheld image capture and pointing device relative to a display assembly may comprise determining a distance from the display assembly to the handheld device. For example as described above with respect to FIGS. 1-9, determining a position of a handheld image capture and pointing device relative to a display assembly may comprise determining an offset angle of the handheld device with respect to a plane intersecting the display assembly, for example a plane intersecting the display at a right angle along a line from the top center of the display assembly to the bottom center of the display assembly.

In this example, for example as described above with respect to FIGS. 1-9, determining an orientation of a handheld image capture and pointing device relative to a display assembly may comprise determining a location in the plane of the display assembly at which the image capture and pointing device is aimed. For example as described above with respect to FIGS. 1-9, determining an orientation of a handheld image capture and pointing device relative to a display assembly may comprise determining rotational orientation of the handheld device, for example a rotational orientation of the device with respect to a line along which the handheld device is aimed.

In this example, in a similar manner as described above with respect to FIGS. 1-9, a system may similarly determine a relative position and/or relative orientation of a handheld image capture and pointing device with respect to another component of system 100 or another component of another system, whether by using the beacon-based determination techniques described above and/or by using one or more of the other position/orientation determination techniques (e.g., gyroscope, accelerometer, compass, video processing) described above. Said determined position and/or orientation relative to one or more other components of a system may similarly be used to control one or more aspects of a GUI comprising one or more captured images displayed on a display.

At block 1012, in this example, the system may update display of the graphical user interface comprising the first image in accordance with the determined position and/or the determined orientation. In the example of system 100, engine 106 may update one or more features or aspects of the GUI comprising the first captured image displayed on display 104*a*.

In this example, updating display of the graphical user interface comprising the first image in accordance with the determined position and/or the determined orientation may comprise controlling a displayed cursor on the GUI, selecting an image for display on the GUI, zooming an image on the GUI, generating an annotation on an image on the GUI, rotating an image on the GUI, resizing an annotation on an image on the GUI, rotating an annotation on an image on the GUI, and/or selecting or updating a display size for an object and/or a font size for text on the GUI.

In this example, updating display of the graphical user interface comprising the first image in accordance with the determined position and/or the determined orientation may comprise displaying a cursor on the graphical user interface at a location on the display at which the handheld device is determined to be aimed. A user may then press one or more buttons on the handheld device to execute a cursor "click" in the GUI.

In this example, updating display of the graphical user interface comprising the first image in accordance with the determined position and/or the determined orientation may comprise generating and displaying an annotation on the displayed image at a location on the display at which the handheld device is determined to be aimed. For example, a user may point the handheld device at a location on the display displaying a tissue feature and the system may generate an annotation (e.g., a displayed, numbered, drawn, and/or labeled bounding box) at the location at which the device is aimed. The user may label one or more regions of interest in an image of tissue in this manner, and the labeled regions of interest may be stored for future review, used for image analysis, and/or used for feature tracking in one or more video streams.

In this example, updating display of the graphical user interface comprising the first image in accordance with the determined position and/or the determined orientation may comprise rotating an image annotation in accordance with the orientation of the handheld device. An image (e.g., the first captured image) displayed on the GUI may be rotated in accordance with rotation of the handheld device. Another feature of the GUI, such as but not limited to an image annotation (e.g., a region of interest bounding box) may be rotated in accordance with rotation of the handheld device.

In this example, updating display of the graphical user interface comprising the first image in accordance with the determined position and/or the determined orientation may comprise modifying a size of a graphical user interface object such as a displayed image and/or an image annotation in accordance with the position of the handheld device. For example, a user may be able to push the handheld device toward the display assembly to decrease the size of the GUI object and pull the handheld device away from the display assembly to increase the size of the GUI object. The system may be configured to automatically set the size of one or more GUI objects (e.g., an image display window, text on the GUI) in accordance with a determined distance of the handheld device from the display assembly, for example to ensure that text is legible by a user of the handheld device when the user is standing at various distances from the display assembly.

In this example, updating display of the graphical user interface comprising the first image in accordance with the determined position and/or the determined orientation may comprise displaying a notification based on an offset angle determined in accordance with the determined position of the handheld device. For example, the system may be configured to display a warning or other notification when handheld device is at an offset angle that determines a predefined threshold offset angle, such that the user may be made aware that his viewing angle is non-optimal.

At block 1014, in this example, the system may, in accordance with the determined position and/or the determined orientation, identify a first region of interest in the first image. In the example of system 100, image processing and display engine 106 may identify the first region of interest. The identified region of interest may be a region of interest that is "tagged" by a user of the handheld device when the user points the handheld device at a portion of the image displaying the region to be tagged and executes an input such as pressing one or more buttons on the handheld device. The system may generate an annotation associated with the tagged region of interest in the image, including by generating and displaying a visual marker such as a bounding box highlighting the annotated region and/or by generating and storing metadata associated with the annotated region, wherein the metadata may include a location in the image, a time of the annotation, an unique identifier of the annotation, a label of the annotation, time stamp data for the annotation, information indicating a user who created the annotation, and/or information indicating a manner in which the annotation was created.

At block 1016, in this example, the system may apply a tracking algorithm and/or an image analysis algorithm to the first region of interest. In the example of system 100, image processing and display engine 106 may apply said tracking algorithm and/or image analysis algorithm.

In this example, an image analysis algorithm applied may determine a type of tissue associated with the first region of interest, a health of tissue associated with the first region of interest, a level of perfusion of tissue associated with the first region of interest, and/or any other medically relevant information that may be discerned from the image of the tissue associated with the first region of interest.

In this example, a tracking algorithm applied may track one or more features of tissue associated with a region of interest across a plurality of video frames of which the first captured image is a part. Thus, a user may tag a tissue feature in the first captured image and the system may track (e.g., automatically locate and identify) the tissue feature across one or more other frames in a video stream from which the first captured image is taken.

In this example, the system may be configured to output data and/or image portions of a portion of tissue in another frame of the video stream wherein the data is based on a portion or portions of the one or more other frames identified by the tracking algorithm. The system may be configured to apply one or more image analysis algorithms to a portion or portions of one or more other frames in the video stream identified by the tracking algorithm.

At block 1018, in this example, the system may capture a second image using an image sensor of the handheld image capture and pointing device. In the example of system 100, image capture and pointing device 102 may capture the second image of tissue of the patient. The second captured image may be a standalone still image; alternatively, the second captured image may be a frame of a series of video frames.

In this example, the second captured image may be an image captured in one or a plurality of spectra in which the image capture device is configured to operate; for example, the captured image may be an IR image. The tissue captured in the second image may be the same tissue as captured in the first image. For example, the image capture device may be configured to use a single set of one or more image sensors sensitive in multiple different spectra to capture both the first and second images, or the image capture device may be configured to use separate sets of one or more image sensors sensitive in different respective spectra to capture the first and second images respectively.

In this example, the tissue may be the same tissue captured in the first image. The second captured image may be captured simultaneously or essentially simultaneously (e.g., within less than or equal to 1 second, 0.1 seconds, 0.01 seconds, or 0.001 seconds) with the first image, such that the first and second images may represent the same tissue area at the same or essentially the same period in time in different spectra. The first and second images may be corresponding frames representing the same or essentially the same moment in time in simultaneously-captured video streams of the target tissue.

In this example, the second captured image may be processed locally and/or transmitted for remote processing. In the example of FIG. 1, the second captured image may be transmitted (by wired or wireless network communication) to image processing and display engine 106 (where it may be processed and/or caused to be displayed by display assembly 104).

At block 1020, in this example, the system may apply a tracking algorithm and/or image analysis algorithm to a second region of interest, wherein the second region of interest is in the second image and corresponds to the first region of interest. Block 1020 may follow from both block 1018 and block 1014. In the example of system 100, image processing and display engine 106 may apply said tracking algorithm and/or image analysis algorithm.

In this example, the system may determine the second region of interest in the second image based on the first region of interest in the first image. For example, when the first and second image depict the same tissue region at the same point in time, the second region of interest may be selected to have the same pixel coordinates in the second image as the pixel coordinates of the first region of interest in the first image.

In this example, the system may be configured to select the second region of interest in the second image based on spatial correspondence with the first region of interest (e.g., as indicated by a user using the pointing device) in the first image, and to then apply a tracking algorithm to a video stream from which the second image was taken to track a tissue feature in multiple frames of the video stream of the second image.

In this example, the system may be configured to select the second region of interest in the second image based on spatial correspondence with a region of interest in a video stream from which the first image was taken. For example, a user may indicate the first region of interest corresponding to a tissue feature in the first image, and the system may then track the tissue feature to a subsequent frame of the first video stream. The system may then correlate the subsequent frame of the first video stream spatially to the second image in the event that the subsequent frame and the second image correspond to the same point in time.

In another example, instead of spatially correlating the first image or the subsequent frame in the first video stream to the second image itself, the system may spatially correlate the first image or the subsequent frame in the first video stream to a prior frame in the second video stream, wherein the prior frame was captured at an earlier time in the second video stream than the second image. The system may use the spatial correlation to identify a tissue feature in the second video stream starting at the prior frame and may apply a tracking algorithm to track the tissue feature in the second video stream to select the second region of interest (corresponding to the tissue feature) in the second image.

It should be noted that image tracking algorithms may be applied with or without regard for a time-direction of frames from a video stream, such that one or more tissue features may be traced forward and/or backward in one or more video streams.

In this example, the system may apply an image analysis algorithm to the second region of interest in the second image once the image analysis algorithm is identified therein. The image analysis algorithm applied may determine a type of tissue associated with the second region of interest, a health of tissue associated with the second region of interest, a level of perfusion of tissue associated with the second region of interest, and/or any other medically relevant information that may be discerned from the image of the tissue associated with the second region of interest.

It may be advantageous to allow a practitioner to tag a region of interest in a first video stream and/or to automatically track a tissue feature in a first stream because the first stream may be more amenable to human and/or automated visual perception at certain points in time. For example, if a first video stream is a white light stream and a second video stream is a fluorescence IR stream, the amount of light captured in the second video stream may be very low when there is not a, e.g. pre-administered, bolus of fluorescence agent traveling through vasculature of the target tissue. Thus, it may be advantageous to track a tissue feature in a white light video stream before the imaging agent is present in the tissue and to then observe the fluorescence video stream of the feature and/or apply one or more image analysis algorithms to the fluorescence video stream of the feature only at the time that the imaging agent is present in the tissue.

Figure 11A:
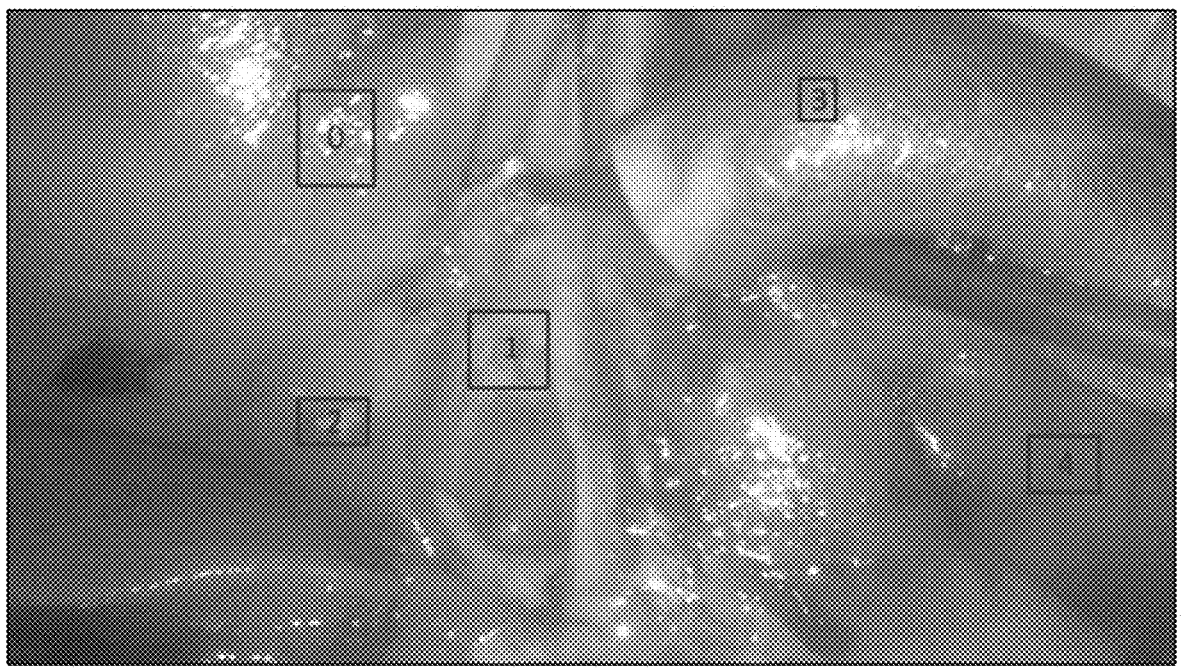
FIGS. 11A and 11B depict annotated medical images in white light and infrared light, respectively, in accordance with some aspects.
Figure 11B:
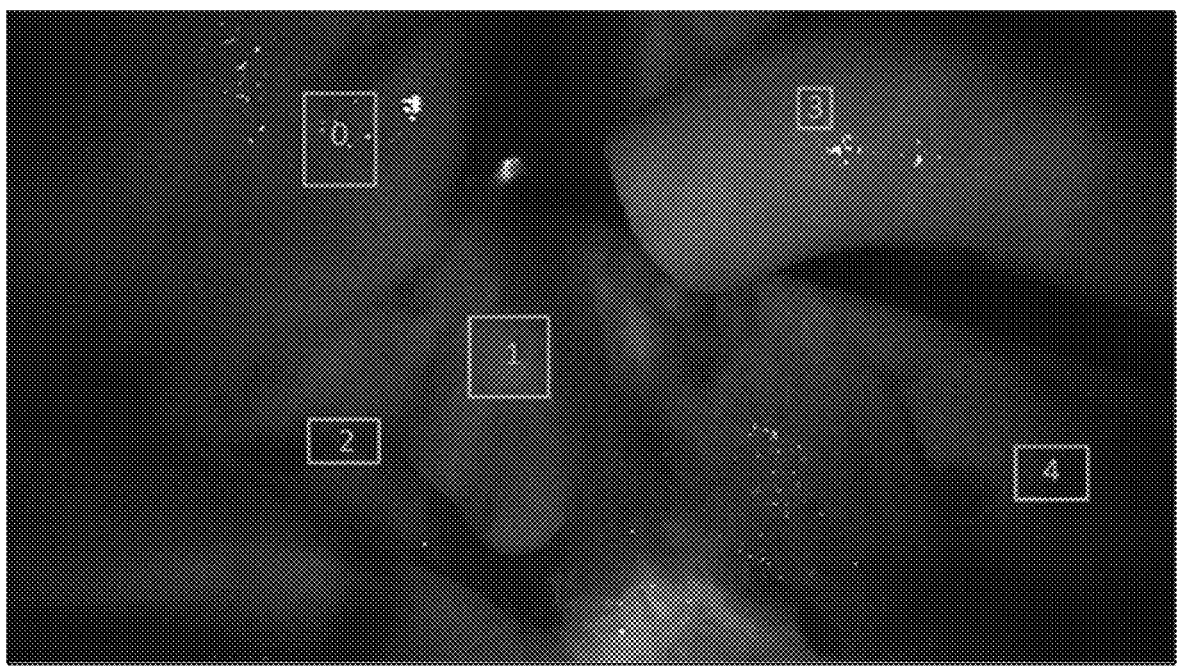

FIGS. 11A and 11B, discussed in further detail below with respect to exemplary tracking techniques and exemplary image annotation techniques, show corresponding annotated images of a target tissue area, wherein the image in FIG. 11A is captured in white light and the image in FIG. 11B is captured in infrared spectrum and rendered in grayscale. As shown, the two images have been annotated with corresponding regions of interest, wherein each image includes regions of interest numbered 1-5 and wherein similarly numbered regions of interest in the images correspond to one another by indicating the same tissue features in both images. Thus, for example, region of interest "1" in the image in FIG. 11A may be the region of interest in the first captured image in method 1000, and region of interest "1" in the image in FIG. 11B may be the region of interest in the second captured image in method 1000.

Exemplary Tracking Techniques

As described above, a system for medical image capture, display, manipulation, annotation, and analysis, such as system 100, may be configured such that two (or more) video streams depicting the same target tissue may be simultaneously captured, wherein a first one of the video streams captures the target tissue in a first spectrum (e.g., white light) and a second one of the video streams captures the target tissue in a second spectrum (e.g., IR). In this example, an object such as a tissue feature may be tracked in one video stream (e.g., a white light video stream) to determine a region of the other video stream (e.g., an IR video stream) at which image analysis should be performed or from which data should be extracted. In this manner, a system may be configured to use frame-synchronized video channels (e.g., video streams) to extract information out of a first channel of video (e.g., a white light video channel) and apply that information to corresponding positions in the second channel of video (e.g., an IR video channel).

Described below are exemplary techniques for performing tracking in frame-synchronized video streams.

In this example, a system may be configured to track a tissue feature in a white light video stream and to then extract information from or analyze a corresponding location in a frame-synchronized IR video stream at a time at which a bolus of fluorescence agent is moving through the tissue vasculature and emitting IR fluorescence emission light. The system may track one or more regions of interest in white light video since white light video may have more information than fluorescence video that is advantageous to the performance of the tracking algorithm. As the white light video sequence continues, the tracking algorithm may lock-onto one or more of these regions of interest and track their coordinates throughout the white light video sequence. The region of interest coordinates that are tracked in the white light video channel may then be used to identify corresponding regions in the IR video channel and to do analysis on (e.g., extract data from and/or perform one or more image analysis techniques on) said corresponding regions and/or visualize said corresponding regions. Thus, tissue tracking may be effectively performed in an information-rich white light spectrum and then fluorescence emission information may be extracted from an IR fluorescence emission spectrum at regions selected by the tracking algorithm.

One or both video feeds used in performance of the tracking techniques described herein may be captured using a handheld image capture and pointing device, such as device 102 of system 100.

The image capture device may be configured to use a single set of one or more image sensors sensitive in multiple different spectra to capture both the first and second video streams. The image capture device may be configured to use separate sets of one or more image sensors sensitive in different respective spectra to capture the first and second video streams respectively. Both sets of one or more sensors may simultaneously capture images of the same target tissue.

In this example, after capturing one or both of the video streams, the image capture device may transmit (e.g., via wired or wireless network communication) the captured video stream(s) to a processing device for application of one or more of the tracking techniques described herein. The tracking techniques described herein may be applied by image processing and display engine 106. Engine 106 may be communicatively coupled to one or more electronic data stores for storing sequences of frames from one or more received video streams. The tracking techniques described herein may be performed in real time as the video streams are received and/or on pre-recorded and stored video streams.

FIGS. 11A and 11B show corresponding annotated images of a target tissue area, wherein the image in FIG. 11A is captured in white light and the image in FIG. 11B is captured in infrared spectrum and rendered in grayscale. As shown, the two images have been annotated with corresponding regions of interest, wherein each image includes regions of interest numbered 1-5 and wherein similarly numbered regions of interest in the images correspond to one another by indicating the same tissue features in both images. Thus, for example, region of interest "1" in the image in FIG. 11A may be a region of interest that is or has been tracked in a white light video stream, and region of interest "1" in the image in FIG. 11B may be a corresponding region in a frame of the IR video stream, selected on the basis of the tracking algorithm applied to the white light video stream, on which the system may perform data extraction or image analysis.

FIG. 12 depicts a flowchart representing an exemplary method 1200 of capturing medical video and identifying regions of interest therein, in accordance with some aspects.

As described below in detail, method 1200 may enable an image capture and display system to capture multiple streams of medical video (e.g., using a handheld image capture and pointing device); to track one or more features of target tissue in a first video stream; to identify, based on said tracking, a region depicting the feature of the target tissue in a second video stream; and to apply one or more image analysis algorithms and/or visualization techniques to the region depicting the feature of the target tissue in the second video stream.

In this example, method 1200 may be carried out, in whole or in part, by one or more of the components of a system for medical image capture, display, manipulation, annotation, and analysis, such as system 100 described above with respect to FIG. 1. Any one or more of the aspects of method 1200 may be combined, in whole or in part, with any one or more of the aspects of FIG. 1, and/or with any one or more of the systems, methods, devices, and/or techniques described elsewhere herein.

At block 1202, in this example, the system may capture a first series of video frames of target tissue in a first spectrum. In the example of system 100, image capture and pointing device 102 may capture the first video stream (e.g., a time series of video frames) of tissue of a patient. The first series of video frames may be captured in one or a plurality of spectra in which the image capture device is configured to operate; for example, the first captured video stream may be a white light video stream.

In this example, the first captured video stream may be processed locally and/or transmitted for remote processing. In the example of FIG. 1, the first captured video stream may be transmitted (by wired or wireless network communication) to image processing and display engine 106 (where it may be processed and/or caused to be displayed by display assembly 104).

At block 1204, in this example, the system may capture a second series of video frames of the target tissue in a second spectrum.

In the example of system 100, image capture and pointing device 102 may capture the second video stream (e.g., a time series of video frames) of tissue of a patient. The second series of video frames may be captured in one or a plurality of spectra in which the image capture device is configured to operate; for example, the second captured video stream may be an IR video stream.

The second captured video stream may be processed locally and/or transmitted for remote processing. In the example of FIG. 1, the second captured video stream may be transmitted (by wired or wireless network communication) to image processing and display engine 106 (where it may be processed and/or caused to be displayed by display assembly 104).

In a similar manner as described above the image capture device may be configured to use a single set of one or more image sensors sensitive in multiple different spectra to capture both the first and second video streams. The image capture device may be configured use separate sets of one or more image sensors sensitive in different respective spectra to capture the first and second video streams respectively. Both sets of one or more sensors may face in the same direction and therefore simultaneously capture video streams of the same target tissue.

In this example, the first and second video streams may be captured simultaneously with one another. Corresponding frames of the first and second video streams may be captured simultaneously or essentially simultaneously (e.g., within less than or equal to 1 second, 0.1 seconds, 0.01 seconds, or 0.001 seconds) with one another, such that the corresponding frame may represent the same tissue area at the same or essentially the same period in time in different spectra. The corresponding frames may thus represent the same or essentially the same moment in time in the simultaneously-captured video streams of the target tissue.

At block 1206, in this example, the system may identify a first region of interest in the first series of video frames, the first region of interest corresponding to a first feature of the target tissue. In the example of system 100, image processing and display engine 106 may identify the first region of interest. The first region of interest may be identified in one or more frames of the first series of video frames. The system may automatically identify the first region of interest (e.g., using one or more image analysis or object recognition algorithms).

The system may identify the first region of interest based at least in part on user input indicating the region in one or more frames of the first series of video frames. A user may use a mouse, keyboard, touch-screen, or other input device to indicate a portion of a displayed image from the first series of video frames, such as by selecting a center of the region of interest or drawing a bounding box (or other bounding shape) for the region of interest. A user may specify the first region of interest by using a handheld image capture and pointing device (e.g., device 100), for example by using said device to point at a portion of an image (e.g., with a cursor) displayed on a display assembly (e.g., display assembly 104) to generate a tag or bounding box or to otherwise cause the system to identify the portion of the image at which the user is pointing as the first region of interest. The system may select the first region of interest based on a portion of a displayed image at which a handheld image capture and pointing device is aimed in accordance with all or part of any of the techniques described above with respect to FIGS. 2-10 and method 1000, for example blocks 1004-1014 of method 1000.

At block 1208, in this example, the system may apply a tracking algorithm to track the first feature of the target tissue in the first series of video frames, wherein the tracking algorithm is configured to track the first feature independently from tracking of surrounding tissue. In the example of system 100, image processing and display engine 106 may apply said tracking algorithm. In this example, the tracking algorithm may be configured to track the first feature through various frames (e.g., forward or backward in time) of the first series of video frames based on the recognition (e.g., by image analysis performed separate from and/or as a part of the tracking algorithm) of the tissue feature in the first region of interest identified by the system in one or more frames of the first series of video frames. Thus, for example, a user may tag the first region of interest containing the tissue feature in one frame of the first video stream, and the system may then track the tissue feature throughout the rest of the first video stream.

In this example, the tracking algorithm configured to track the first feature independently from tracking of surrounding tissue may be (or may include) a Discriminative Correlation Filter. The Discriminative Correlation Filter may be a Discriminative Correlation Filter with Channel and Spatial Reliability. The algorithm may be a video processing (e.g., computer vision) type of algorithm. The tracking algorithm may include one or more machine learning components.

The system may be configured to track every pixel in a frame using a dense optical flow approach. In this approach, the system may track the movement (e.g., motion vectors) of every pixel through the video sequence. The system may track the motion of every pixel without considering one or more ROI's with respect to motion tracking. A visible light series of video frames may still be used to determine the corresponding positions in a corresponding IR series of video frames.

At block 1210, in this example, the system may identify a second region of interest in the second series of video frames, based on the tracking algorithm applied to the first series of video frames, the second region of interest corresponding to the first region of interest. In the example of system 100, the identification of the second region of interest may be performed by image processing and display engine 106. The system may be configured to select the second region of interest in a frame of the second series of video frames based on spatial correspondence with the first region of interest and/or based on spatial correspondence to the first tissue feature that may be tracked throughout the first series of video frames. For example, a user may indicate the first region of interest corresponding to the tissue feature in one or more frames of the first series of video frames, and the system may then track the tissue feature to a different frame of the first series of video frames. The system may then correlate the different frame from the first series of video frames spatially to a frame from the second series of video frames.

Spatial correspondence may be used between time-synchronized frames—e.g., frames representing the same or essentially the same moment in time—across the different series of video frames. Spatial correspondence of regions of interest may refer to regions of interest in time-synchronized frames that have the same or similar pixel coordinates in the frames. For example, in the example of FIGS. 11A and 11B, the pair of regions of interest labeled "1" in the respective images have a spatial correspondence with one another, as do the pairs labeled "2," "3," "4," and "5." Thus, as used herein in describing method 1200, it should be understood that the "first region of interest" and the "second region of interest" may depict a similar or identical tissue area in different images.

Tracking of a tissue feature in a region of interest may be performed before and/or after assessing one or more spatial correspondences to identify the second region of interest in a frame of the second video stream. For example, a user may indicate the first region of interest containing the tissue feature in a first frame of the first video stream. The system may determine a spatially corresponding second region of interest in a first time-synchronized frame of the second video stream (that is time-synchronized with the first frame in the first stream). The system may first track the tissue feature to a second video frame in the first video stream, and the system may then determine the spatially corresponding second region of interest in a second time-synchronized frame of the second video stream (that is time-synchronized with the second frame in the first stream). The system may then optionally perform additional tracking on the tissue feature in one or both of the first and second streams after the identification of the second region of interest.

At block 1212, in this example, the system may apply an image analysis algorithm to the second region of interest. At block 1214, in this example, the system may visualize the second region of interest. One or both of block 1212 and block 1214 may be performed following block 1210 and the identification of the second region of interest in one or more frames of the second series of video frames. In the example of system 100, image analysis may be performed by image processing and display engine 106 and visualization may be performed by image processing and display engine 106 causing display 104*a* of display assembly 104 to display the second region of interest.

In this example, the system may be configured to output data and/or image portions of the second region of interest. The system may be configured to apply one or more image analysis algorithms to the second region of interest. An image analysis algorithm applied may determine a type of tissue associated with the second region of interest, a health of tissue associated with the second region of interest, a level of perfusion of tissue associated with the second region of interest, and/or any other medically relevant information that may be discerned from the second region of interest.

In method 1200, the system may be configured such that image tracking may be performed in white light at a time before fluorescence agent is present in the target tissue, and then image analysis or visualization or information extraction may be performed in IR light at a time when a fluorescence agent emitting IR agent is present in the vasculature of the target tissue.

For example, the first and second series of video frames may be captured during a first period of time during which a fluorescence dye is not present in the target tissue and a second period of time during which the fluorescence dye is present in the target tissue; the tracking algorithm may be applied to a first set of frames, corresponding to both the first period of time and the second period of time, from the first series of video frames; and the one or more frames of the second series of video frames to which an image analysis algorithm is applied may correspond to the second period of time. The one or more frames of the first series of video frames in which the first region of interest is identified may correspond to the first period of time.

In this example, for example as shown in FIGS. 11A and 11B, the system may be configured to simultaneously track multiple different regions of interest and/or multiple different tissue features in a single video stream (and/or in a single set of frame-synchronized video streams). Two or more of the tracked regions or tracked features may be tracked independently of surrounding tissue.

Exemplary Image Annotation Techniques

As described above, a system for medical image capture, display, manipulation, annotation, and analysis, such as system 100, may be configured to capture a medical image and to generate annotation data to be stored in association with a region of interest in the medical image and/or in association with a tissue sample extracted from the tissue at an area indicated by the region of interest in the image. The medical image can be obtained by an operator of the system before, during, or after a medical practitioner extracts the tissue sample. The system may be configured to capture a medical image and to generate annotation data to be stored in association with a region of interest in the medical image and/or in association with a tissue sample that has been extracted, or is about to be extracted, from the tissue at an area indicated by the region of interest in the image. A system may capture a medical image (e.g., a frame from a medical video) using a handheld image capture and pointing device, display the captured medical image on a display assembly, determine a location in said image displayed on said display assembly at which the handheld device is pointed, and generate and store annotation data associated with a region of interest defined in the image at the location at which the handheld device is pointed.

During a medical/surgical procedure, a surgeon or other practitioner may capture an image from a video stream (e.g., a live video stream being captured by a handheld image capture device such as device 102) shortly before the practitioner intends to remove a tissue sample for analysis. Once the image is captured, the practitioner may then mark one or more regions of interest in that image such that the regions of interest and any associated metadata may be associated with the tissue sample to be taken. The captured image and data associated with the region of interest may be stored in association with the tissue sample to be removed. Alternatively, or additionally, the practitioner may then remove the tissue sample from the anatomy and the captured image and data associated with the region of interest may be stored in association with the removed tissue sample and/or in association with any data generated from analysis of the removed tissue sample.

Examples of images annotated with regions of interest are shown in FIGS. 11A and 11B, with FIG. 11A showing a white light image and FIG. 11B showing an IR image rendered in grayscale, with both images having five regions of interest marked thereon.

In this example, one or more regions of interest may be marked in response to a user executing a user input indicating a portion of the image at which the region of interest should be marked.

In this example, the system may identify the region of interest based at least in part on user input indicating the region in the image using a mouse, keyboard, touch-screen, or other input device to indicate a portion of the displayed image, such as by selecting a center of the region of interest or drawing a bounding box (or other bounding shape) for the region of interest. A user may specify the region of interest by using a handheld image capture and pointing device (e.g., device 100), for example by using said device to point at a portion of an image (e.g., with a cursor) displayed on a display assembly (e.g., display assembly 104) to generate a tag or bounding box or to otherwise cause the system to identify the portion of the image at which the user is pointing as the region of interest. The system may select the first region of interest based on a portion of a displayed image at which a handheld image capture and pointing device is aimed in accordance with all or part of any of the techniques described above with respect to FIGS. 2-10 and method 1000, for example blocks 1004-1014 of method 1000. The identified region of interest may be a region of interest that is "tagged" by a user of the handheld device when the user points the handheld device at a portion of the image displaying the region to be tagged and executes an input such as pressing one or more buttons on the handheld device.

The system may generate an annotation associated with the tagged region of interest in the image, including by generating and displaying a visual marker such as a bounding box highlighting the annotated region and/or by generating and storing metadata associated with the annotated region, wherein the metadata may include a location in the image, a time of the annotation, an unique identifier of the annotation, a label of the annotation, time stamp data for the annotation, information indicating a user who created the annotation, and/or information indicating a manner in which the annotation was created.

The system may be configured to accept one or more inputs from a user of the system to generate and store metadata associated with the region of interest. One or more of these inputs may be input to the system using a microphone (e.g., for voice input), mouse, keyboard, touch-screen, or the like. One or more of these inputs may be input to the system using a handheld image capture and pointing device (e.g., device 100), including by using one or more buttons, keys, microphones, touch-screen devices, or the like mounted thereon. One or more of these inputs may be input to the system using a handheld image capture and pointing device (e.g., device 100), including by generating metadata based at least in part on a determined location and/or orientation of the handheld device (e.g., relative to a display assembly) at the time the annotation and/or metadata are created.

Time stamp metadata associated with an annotation (e.g., region of interest) may include time-stamp data indicating a time at which the image (e.g., video frame) was captured and/or time-stamp data indicating a time at which the annotation was created or updated.

In this example, the system may be configured to automatically generate a unique identifier for each of a plurality of regions of interest generated by the system. The system may automatically increment a unique identifier each time the system creates a new annotation. Unique identifiers may be unique across a surgical procedure, a set of surgical procedures, a patient's medical history, a medical practitioner's professional history, a hospital, a surgical system or platform, and/or a laboratory.

Tissue samples before being sent to pathology may be labeled with the labels from the region of interest where the sample was taken. Once the pathology results are received, the same label may be used to correlate the pathology results to the regions of interest as well as the image of the anatomy and the time stamp in the video from which the image was taken.

The region of interest coordinates may then be tracked in the white light video channel and may then be used to analyze and/or visualize corresponding regions in the IR video channel, for example as discussed above with respect to method 1200.

FIG. 13 depicts a flowchart representing an exemplary method 1200 of annotating medical images, in accordance with some aspects.

As described below in detail, method 1300 may enable an image capture and display system to capture a medical image (e.g., a frame from a medical video) using a handheld image capture and pointing device; to display said medical image on a display assembly; to determine a location in said image displayed on said display assembly at which the handheld device is pointed; and to generate and store annotation data associated with a region of interest defined in the image at the location at which the handheld device is pointed.

In this example, method 1300 may be carried out, in whole or in part, by one or more of the components of a system for medical image capture, display, manipulation, annotation, and analysis, such as system 100 described above with respect to FIG. 1. Any one or more of the aspects of method 1300 may be combined, in whole or in part, with any one or more of the aspects of FIG. 1, and/or with any one or more of the systems, methods, devices, and/or techniques described elsewhere herein.

At block 1302, in this example, the system may capture a first image in a first spectrum using a handheld image capture and pointing device. In the example of system 100, image capture and pointing device 102 may capture an image of tissue of a patient. The first captured image may be a standalone still image; alternatively, the first captured image may be a frame of a series of video frames. The first captured image may be an image captured in one or a plurality of spectra in which the image capture device is configured to operate; for example, the captured image may be a white light image.

The first captured image may be processed locally and/or transmitted for remote processing. In the example of FIG. 1, the first captured image may be transmitted (by wired or wireless network communication) to image processing and display engine 106 (where it may be processed and/or caused to be displayed by display assembly 104).

In this example, capturing the image at block 1302 may share any one or more characteristics in common with capturing an image as described above with reference to block 1002 of method 1000.

At block 1304, in this example, the system may display the first image using a display of a display assembly. In the example of system 100, the image may be displayed by image processing and display engine 106 causing display 104a of display assembly 104 to display the captured image.

Displaying the image at block 1304 may share any one or more characteristics in common with displaying a captured image as described above with reference to block 1004 of method 1000.

At block 1306, in this example, while the first image is displayed on the display of the display assembly, the system may determine a location on the display assembly at which the handheld image capture device is aimed, wherein the location on the display assembly corresponds to a region in the first image, wherein the region in the first image comprises a target tissue area. In the example of system 100, said determination may be made by image processing and display engine 106. The system may make said determination based on one or more sensors onboard the handheld device (e.g., gyroscope, accelerometer, compass), based on video processing of video captured by the handheld device, and/or based on optically detecting and analyzing light emitted by one or more beacons of the display assembly on which the image is displayed. Making said determination may share any one or more characteristics in common with determining a location at which a handheld device is aimed as described above with reference to FIGS. 2-9 and blocks 1006-1010 of method 1000.

At block 1308, in this example, the system may, in response to detecting a user input and determining the location on the display assembly, generate and store annotation data associated with the target tissue area. In the example of system 100, image processing and display engine 106 may detect a user input, such as a button on handheld device 102 or elsewhere being pressed, and may responsively generate and store annotation data associated with the target tissue area. As discussed above, the annotation data may include a bounding box or other indication of the portion of the image corresponding to the region of interest and may further include metadata regarding the tissue area, procedure, patient, practitioner, time stamp data, label data, and/or unique identifier data. Said annotation data may be stored in association with and/or as a part of the annotated image and/or a video of which the annotated image is a frame.

Blocks 1310 and 1318 describe how method 1300 may include frame-synchronized tracking techniques similar to those described above with respect to method 1200. For example, a tissue feature associated with a region of interest that is tagged for tissue tracking by a surgeon may be tracked in video and/or analyzed/visualized in a corresponding video in a different spectrum using the same or similar techniques as described above with respect to method 1200.

At block 1310, in this example, the system may capture a second image in a second spectrum using the handheld image capture and pointing device. In the example of system 100, image capture and pointing device 102 may capture the second image of tissue of the patient. The second image may be an image captured in a different spectrum than the first image; for example, the second image may be an IR image. Capturing the second image at block 1310 may share any one or more characteristics in common with capturing a captured image as described above with reference to block 1018 of method 1000.

At block 1312, in this example, the system may, in response to detecting a user input and determining the location on the display assembly, identify a region of interest in one or more frames of a series of video frames of which the second image is a part, and apply an image analysis algorithm, data extraction operation, and/or visualization operation to the region of interest in the one or more frames of the series of video frames of which the second image is a part. In the example of system 100, said user input detection, region identification, image analysis, data extraction, and/or visualization may be performed by image processing and display engine 106. A surgeon or other practitioner may accordingly tag a region of interest in a frame of a white light video, and the system may then track a tissue feature in the region of interest in the white light video and determine a spatially corresponding region in one or more frames of a frame-synchronized IR video for visualization, data extraction, and/or analysis of the IR video.

Exemplary Computer

FIG. 14 illustrates a computer, in accordance with some aspects. Computer 1400 can be a component of a system for medical image capture, display, manipulation, annotation, and/or analysis, such as system 100 and/or any of its subcomponents described above with respect to FIG. 1. Computer 1400 may be configured to execute a method for medical image capture, display, manipulation, annotation, and/or analysis, such as all or part of any one or more of methods 1000, 1200, and 1300 described above with respect to FIGS. 10, 12, and 13.

Computer 1400 can be a host computer connected to a network. Computer 1400 can be a client computer or a server. As shown in FIG. 14, computer 1400 can be any suitable type of microprocessor-based device, such as a personal computer; workstation; server; or handheld computing device, such as a phone or tablet. The computer can include, for example, one or more of processor 1410, input device 1420, output device 1430, storage 1440, and communication device 1460.

Input device 1420 can be any suitable device that provides input, such as a touch screen or monitor, keyboard, mouse, or voice-recognition device. Output device 1430 can be any suitable device that provides output, such as a touch screen, monitor, printer, disk drive, or speaker.

Storage 1440 can be any suitable device that provides storage, such as an electrical, magnetic, or optical memory, including a RAM, cache, hard drive, CD-ROM drive, tape drive, or removable storage disk. Communication device 1460 can include any suitable device capable of transmitting and receiving signals over a network, such as a network interface chip or card. The components of the computer can be connected in any suitable manner, such as via a physical bus or wirelessly. Storage 1440 can be a non-transitory computer-readable storage medium comprising one or more programs, which, when executed by one or more processors, such as processor 1410, cause the one or more processors to execute methods described herein, such as all or part of any one or more of methods 1000, 1200, and 1300 described above with respect to FIGS. 10, 12, and 13.

Software 1450, which can be stored in storage 1440 and executed by processor 1410, can include, for example, the programming that embodies the functionality of the present disclosure (e.g., as embodied in the systems, computers, servers, and/or devices as described above). Software 1450 can be implemented and executed on a combination of servers such as application servers and database servers.

Software 1450 can also be stored and/or transported within any computer-readable storage medium for use by or in connection with an instruction execution system, apparatus, or device, such as those described above, that can fetch and execute instructions associated with the software from the instruction execution system, apparatus, or device. In the context of this disclosure, a computer-readable storage medium can be any medium, such as storage 1440, that can contain or store programming for use by or in connection with an instruction execution system, apparatus, or device.

Software 1450 can also be propagated within any transport medium for use by or in connection with an instruction execution system, apparatus, or device, such as those described above, that can fetch and execute instructions associated with the software from the instruction execution system, apparatus, or device. In the context of this disclosure, a transport medium can be any medium that can communicate, propagate, or transport programming for use by or in connection with an instruction execution system, apparatus, or device. The transport-readable medium can include, but is not limited to, an electronic, magnetic, optical, electromagnetic, or infrared wired or wireless propagation medium.

Computer 1400 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Computer 1400 can implement any operating system suitable for operating on the network. Software 1450 can be written in any suitable programming language, such as C, C++, Java, or Python. In various aspects, application software embodying the functionality of the present disclosure can be deployed in different configurations, such as in a client/server arrangement or through a Web browser as a Web-based application or Web service, for example.

The foregoing description, for the purpose of explanation, has been described with reference to specific aspects. However, the illustrative discussions above are not intended to be exhaustive or to limit the invention to the precise forms disclosed. Many modifications and variations are possible in view of the above teachings. The aspects were chosen and described in order to best explain the principles of the techniques and their practical applications. Others skilled in the art are thereby enabled to best utilize the techniques and various aspects with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. An image capture and display system for tissue sample tracking, comprising:
a handheld image capture and pointing device;
a display assembly configured to display one or more images captured by the handheld device; and
one or more processors configured to cause the system to:
capture, by the image capture and pointing device, an image;
display, by a display of the display assembly, the image;
while the image is displayed by the display, determine a location on the display assembly at which the handheld device is aimed, wherein the location on the display corresponds to a region in the displayed image, wherein the region in the displayed image comprises a target tissue area; and
in response to detecting a user input and determining the location on the display assembly, generate and store annotation data associated with the target tissue area.

2. The system of claim 1, wherein the annotation data comprises data indicating a region of interest in the image.

3. The system of claim 1, wherein the annotation data comprises a label for the target tissue area generated based on the user input.

4. The system of claim 1, wherein the annotation data comprises time-stamp data generated based on a time-stamp of the image displayed on the display assembly.

5. The system of claim 1, wherein the annotation data comprises a unique identifier automatically generated by the system.

6. The system of claim 1, wherein the annotation data is stored in association with a tissue sample taken from the target tissue area.

7. The system of claim 1, wherein the annotation data is stored in association with pathology results data associated with the tissue sample taken from the target tissue area.

8. The system of claim 1, wherein:
the image is captured by the image capture and pointing device, as part of a first time series of video frames of the target tissue in a first spectrum; and
the one or more processors cause the system to:
capture, by the image capture and pointing device, a second time series of video frames of the target tissue in a second spectrum; and
in response to detecting a user input and in accordance with the determined location on the display assembly, identify a region of interest in one or more frames of the second series of video frames and apply an image analysis algorithm to the region of interest in the one or more frames of the second series of video frames.

9. A non-transitory computer-readable storage medium for image capture and display for tissue sample tracking, the non-transitory computer-readable storage medium storing instructions configured to be executed by one or more processors of a system for image capture and display for tissue sample tracking comprising a handheld image capture and pointing device and a display assembly configured to display one or more images captured by the handheld device, wherein executing the instructions causes the system to:
capture, by the image capture and pointing device, an image;
display, by a display of the display assembly, the image;
while the image is displayed by the display, determine a location on the display assembly at which the handheld device is aimed, wherein the location on the display corresponds to a region in the displayed image, wherein the region in the displayed image comprises a target tissue area; and
in response to detecting a user input and determining the location on the display assembly, generate and store annotation data associated with the target tissue area.

10. A method for image capture and display for tissue sample tracking, the method performed at a system for image capture and display for tissue sample tracking comprising a handheld image capture and pointing device, a display assembly configured to display one or more images captured by the handheld device, and one or more processors, the method comprising:

capturing, by the image capture and pointing device, an image;

displaying, by a display of the display assembly, the image;

while the image is displayed by the display, determining a location on the display assembly at which the handheld device is aimed, wherein the location on the display corresponds to a region in the displayed image, wherein the region in the displayed image comprises a target tissue area; and in response to detecting a user input and determining the location on the display assembly, generating and storing annotation data associated with the target tissue area.

\* \* \* \* \*